(12) United States Patent
Wang

(10) Patent No.: US 6,648,024 B2
(45) Date of Patent: Nov. 18, 2003

(54) TUBULAR PRODUCT

(76) Inventor: James C. Wang, 18 Baldwin La., Bluffton, SC (US) 29910

( * ) Notice: Subject to any disclaimer, the term of this patent is extended or adjusted under 35 U.S.C. 154(b) by 0 days.

(21) Appl. No.: 09/976,795

(22) Filed: Oct. 12, 2001

(65) Prior Publication Data

US 2002/0119264 A1 Aug. 29, 2002

Related U.S. Application Data

(63) Continuation-in-part of application No. 09/792,941, filed on Feb. 26, 2001.
(60) Provisional application No. 60/273,679, filed on Mar. 5, 2001, provisional application No. 60/273,753, filed on Mar. 5, 2001, and provisional application No. 60/273,754, filed on Mar. 5, 2001.

(51) Int. Cl.[7] .............................. F16L 9/00; A61M 25/00
(52) U.S. Cl. ........................ 138/177; 138/178; 604/523
(58) Field of Search ..................... 138/177, 178; 604/523, 524, 525; 264/558, 555

(56) References Cited

U.S. PATENT DOCUMENTS

| | | | | |
|---|---|---|---|---|
| 3,312,583 A | * | 4/1967 | Rochlis | |
| 4,282,876 A | * | 8/1981 | Flynn | 604/529 |
| 4,385,635 A | * | 5/1983 | Ruiz | 600/435 |
| 4,904,431 A | * | 2/1990 | O'Maleki | 264/103 |
| 5,085,649 A | * | 2/1992 | Flynn | 604/524 |
| 5,258,160 A | * | 11/1993 | Utsumi et al. | 264/558 |
| 5,533,985 A | * | 7/1996 | Wang | 600/433 |
| 5,542,937 A | * | 8/1996 | Chee et al. | 604/523 |
| 5,622,665 A | * | 4/1997 | Wang | 264/150 |
| 5,695,789 A | | 12/1997 | Harris | 425/131.1 |
| 5,725,814 A | | 3/1998 | Harris | 264/40.3 |
| 6,135,992 A | * | 10/2000 | Wang | 604/525 |
| 6,240,231 B1 | | 5/2001 | Ferrera et al. | 385/115 |

* cited by examiner

*Primary Examiner*—Patrick Brinson
(74) *Attorney, Agent, or Firm*—Squire, Sanders & Dempsey, L.L.P.

(57) ABSTRACT

Manufacturing variable and/or singular property products, such as a tubing, in a tip-and-die assembly, where intermittent acting material injectors are used. Two or more injectors take turns making material shots to maintain a continuous material stream. A singular flow controller regulates the flow for all material streams coming from the injectors.

52 Claims, 17 Drawing Sheets

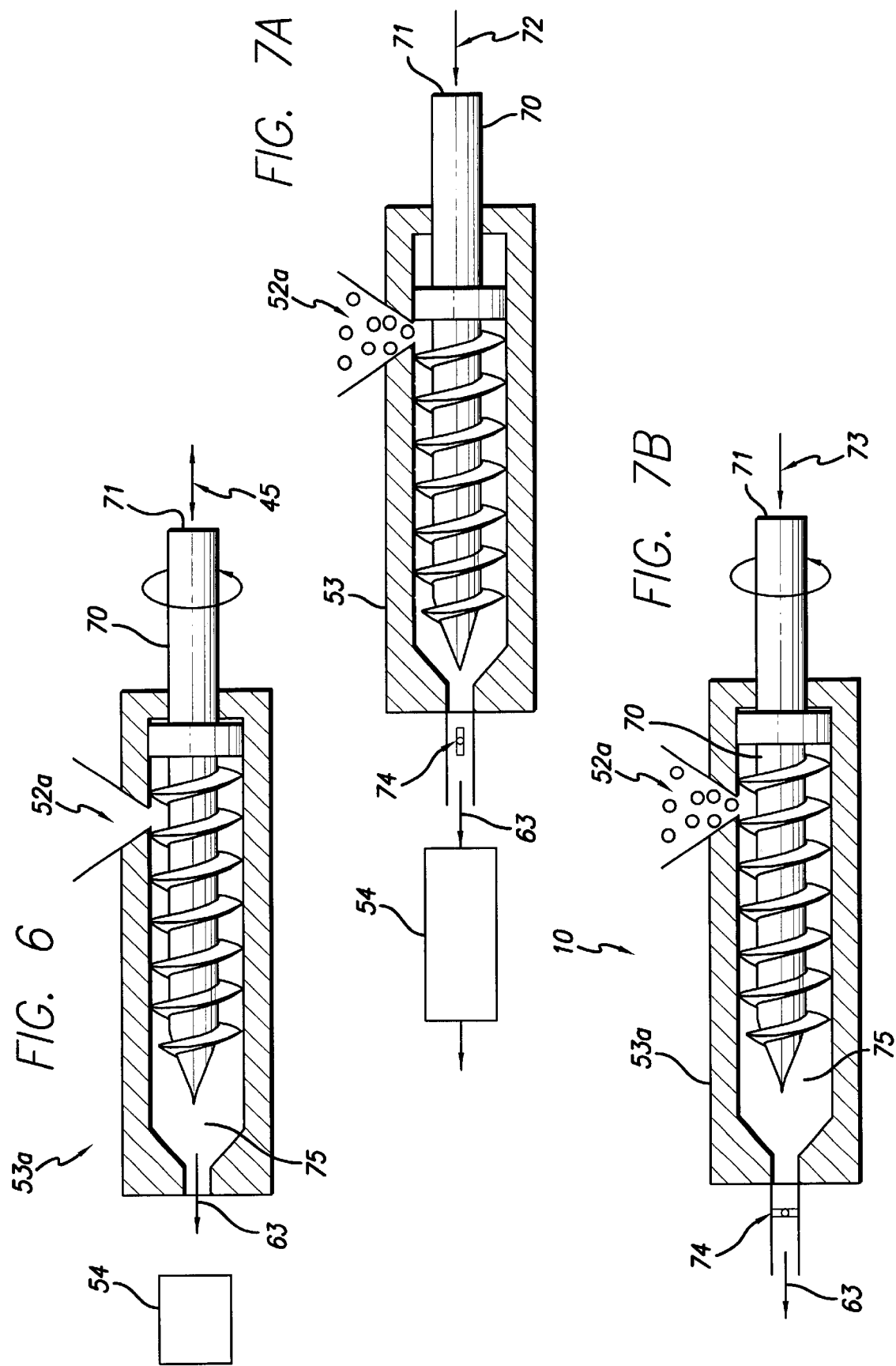

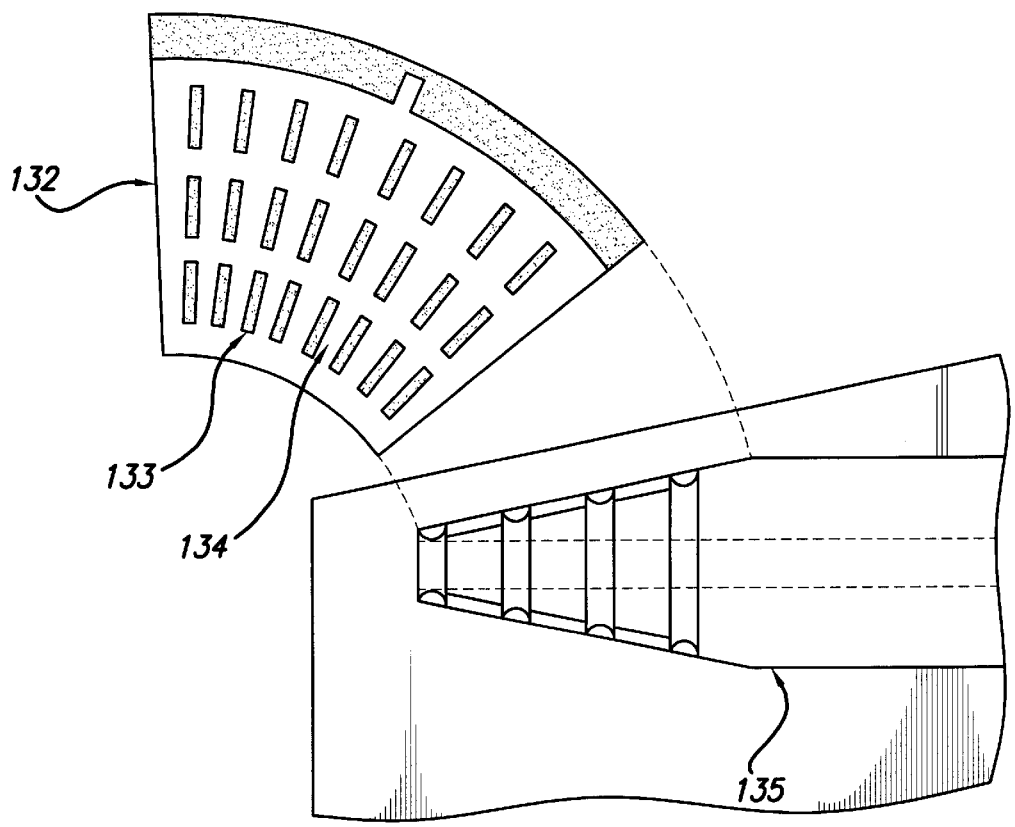
FIG. 20A
FIG. 20B
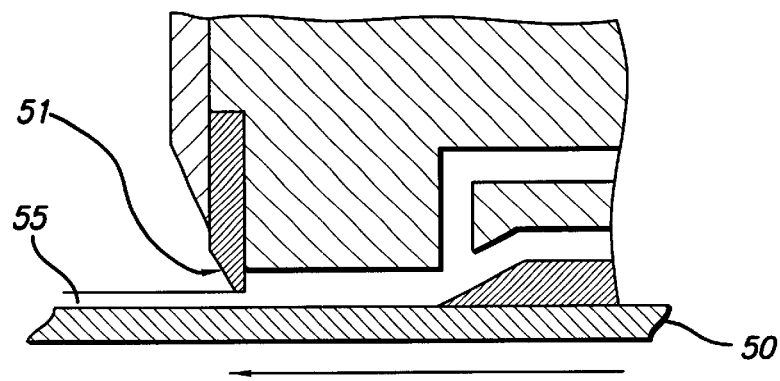
FIG. 27
PRIOR ART

TUBULAR PRODUCT

The present Application is a CIP of Ser. No. 09/792,941, filed Feb. 26, 2001, and entitled "FOLDABLE ELECTRIC CORD ARRANGEMENT AND MANUFACTURE"; and Provisional Application Ser. Nos. 60/273,679; 60/273,753; 60/273,754, filed Mar. 5, 2001, the contents of which are all incorporated by reference herein.

BACKGROUND OF THE INVENTION

Field of the Invention

General Background and State of the Art

This invention relates to variable-property products, and methods for making such products.

A variable-property product is an article that has varied material properties such as stiffness and/or surface frictions and/or elasticity. As an example, medical catheters may be constructed with variable stiffness properties. These catheters have been developed to have different degrees of flexibility throughout their length to satisfactorily meet the requirements of flexibility and also stiffness for manipulation.

Variable stiffness products are currently made with a special extrusion process, called Interrupted Layer Co-extrusion (herein ILC), for making long articles with variable-stiffness properties. U.S. Pat. Nos. 5,533,985 and 5,622,665 describe the ILC process in detail. The contents of each of these patents and all other patents mentioned in this disclosure are hereby incorporated by reference in their entireties.

The prior art processes use a "tip-and-die" assembly to make long articles such as tubing. A "non-pressure-die" set-up requires the tip to extend to the end of the co-extrusion head, flush with, or beyond the face of the die. In a "pressure-die" set-up, the tip is recessed in relation to the die.

In the ILC process, extruded products such as tubing and electrical cables are manufactured with commonly used rotating extruders. The polymer streams that come from the extruders are then fed through modulators. Usually there are two modulators for every variable-stiffness material stream (polymer stream). The main modulator is to direct the polymer flow and the relief modulator is to reduce the residual flow. In the prior art process, first, the polymer is directed to the co-extrusion head to form the product. Next, the polymer is directed to bleed to the floor as the waste material.

Although the ILC process works well in making some variable-material products, there are a number of problems. In the ILC process, roughly one pound of scrap is generated for every pound of catheters made for a two-polymer system in some cases. The bleeding scrap rate worsens to four pounds of scrap per one pound of products, in some five-polymer systems envisioned. This compares with the normal scrap rate of only 0.1 pound of scrap per pound of goods in a typical extrusion operation. Much of the scrap in an ILC process is generated through bleeding.

Further problems in the ILC process are poor yield for some products, due to such things as modulator breakdowns, solidifying of bleeds, etc. Fluctuations in bleeding can also lead to less than desired repeatability. With hot polymer bleeding to the production floor at all times, the operation of the ILC process is quite messy.

For some more critical products, the transition section from a two-polymer system is not pliable enough. Yet, it is impractical to use more than three polymers in the ILC process, because that would require the use of too many unreliable modulators.

In prior art processes for developing variable stiffness extruded products such as tubing, the products are prone to collapsing upon bending stress, also known as "chinking," more easily at certain points in the transition sections between the different materials.

The transitional chinking problem is due to a thin, stiff tail layer of material in the transition section. The thin stiff layer is the natural result of the polymer flow in the head of the extrusion device. In the prior art, when the stiffness ratio between the stiff polymer and the flexible polymer exceeds a certain value, the composite structure tends to chink. This chinking phenomenon is especially acute for thin walled products, such as catheters.

Another drawback of the prior art processes is the time wasting practice in changing the transition length of a product. To change the transition length, the line must be shut down, the parts changed, and the line started up again to see if the new transition length is satisfactory. If the transition length is unsatisfactory, the same steps have to be repeated over again until the right length is found. This is a very time consuming practice.

In the prior manufacturing process for variable-material products, one of the main drawbacks is that an excessive amount of core scrap is generated. Most core scrap is generated in the purge duration of a manufacturing cycle. In the purge duration, the residual stiff material is purged out by the flexible material so the next production duration of the manufacturing cycle can begin.

To reduce core scrap, the flexible polymer flow rate should be increased to quickly purge out the residual stiff polymer, and the core movement should be significantly slowed down during purging, to use less core material. Unfortunately, this cannot be effected in the prior art. It is well known in extrusion processes, such as the ILC process, for making elongated articles such as tubing or electrical wires, that the speed of the core movement has to closely match the polymer flow rate. In other words, when the polymer flow rate is increased, the core movement has to speed up. The polymer flow rate cannot be increased while simultaneously slowing down the core movement. This is especially true when thin polymer walled products, such as catheters, are involved.

The problem in the prior art exists because when a certain tip and die assembly, such as a pressure-die set-up, is used to make thin polymer walled products, the core speed largely controls the polymer flow rate in the main channel. Simply, the higher the core speed, the more polymer it drags out through the die opening, and the more polymer flows through the main channel.

INVENTION SUMMARY

One aspect of the present invention is to develop a method of forming variable-property material such as tubing, which eliminates the vast amount of bleeding waste of polymers that occurs in prior art processes.

Another aspect of the present invention to make pliable products that contain three or more polymers.

Yet another aspect of the present invention is to develop a process better suited for repeatability, better consistency and fewer breakdowns.

A further aspect of the present invention is to develop a process with improved general cleanliness.

These and other aspects are achieved by the process of the present invention which, in accordance with a broad structural aspect of the invention, includes material injectors, instead of commonly used extruders, used in the prior art ILC process to push material through a tip-and-die head. Prior art extruders deliver steady streams of polymers at constant rates while injectors deliver intermittent shots of polymers at controlled pressures.

Two or more injectors take turns making polymer 'shots' to maintain a continuous polymer stream. In one form of the invented polymer injector, high pressure is exerted at the back of a reciprocating screw which forces the screw to move forward through the injector to send a shot of material, such as molten polymer, out of the injector. The pressure at the back of the screw is then reduced to eliminate the residual flow. The screw then rotates and slowly moves back to replenish the molten polymer in the injector.

The present invention includes the novel use of a singular flow controller for all material streams coming from the injectors.

In one form of the invention for making variable-property products, such as variable-stiffness products, the present invention uses two or more intermittent acting injectors to make continuous articles such as tubing, cables, wires, etc. Preferably, the present invention uses a tip-and-die assembly such as a pressure-die setup in combination with the injectors, drastically reducing the inherent problem of lack of precise control over polymer flow rates for injectors.

In prior art ILC processes, half of the modulators are used for reducing residual flows coming from the extruders. In the present invention, half of the modulators are eliminated in the pressure reduction step of the injectors. The other half of the modulators is replaced by a singular flow controller.

One other aspect of the present invention is to provide a method of forming variable-property material such as tubing which eliminates the chinking that occurs in the prior art processes.

Another aspect of the present invention is to provide a method of forming variable-property material such as a medical catheter which has a more flexible distal section.

It is a further aspect of the present invention to provide a process better suited for changing the transition length of a product, in a less time consuming manner than in the prior art.

These and other aspects are achieved by the present invention which, in accordance with a broad structural aspect of the invention, includes a blending feature in the head of the device which intensely mixes material together as it passes through it. The product that results from the present invention has a transition section comprised of a blend of different types of material.

In an exemplary embodiment for making variable-property products, such as variable-stiffness products, the present invention uses a blending feature in the head of a device to make products such as tubing or electrical wires, where the variable property materials are intensely mixed together to form the new type of transition section shown.

In another aspect of the present invention, a method of forming a variable-property product such as tubing, in a tip and die assembly, allows for a much-increased material flow during the purging process than in prior art.

In another aspect of the present invention, a method of forming a variable-property product such as tubing, in a tip and die assembly, allows for a much increased material flow and a much slowed core speed at the same time, during the purging process, to reduce core scrap.

In yet another aspect of the present invention, a method of forming a variable-property product such as differential-stiffness tubing, in a tip and die assembly, allows for a much more flexible distal section in the product.

In a further aspect of the present invention, a method of forming a variable-property product such as variable stiffness tubing, using a tip and die assembly, allows for the elimination of the thin residual stiff layer that is usually left on the surface of the flexible section of a variable stiffness tubing.

These and other aspects are achieved by the present invention which, in accordance with a broad structural aspect of the invention, includes a diverting feature in the head of a tip and die assembly which allows for a simultaneous increase in material flow and a decrease in core speed.

Other objects and advantages of the present invention will become more apparent to those persons having ordinary skill in the art to which the present invention pertains from the foregoing description taken in conjunction with the accompanying drawings.

BRIEF DESCRIPTION OF THE DRAWINGS

FIG. 6 shows a material injector;

FIG. 7 illustrates, a typical cycle of a material injector;

FIG. 20a shows a tip surface of the polymer blending head opened up and laid flat;

FIG. 20b shows a cross sectional view of the tip in FIG. 10a;

FIG. 27 shows polymer flow paths near the die in a prior art tip and die mechanism;

FIG. 29a shows part of the production cycle of the prior art tip and die process for making an elongated product such as tubing;

FIG. 29b shows part of the production cycle of the prior art tip and die process for making an elongated product such as tubing;

FIG. 29c shows part of the production cycle of the prior art tip and die process for making an elongated product such as tubing;

FIG. 29d shows part of the purging cycle of the prior art tip and die process for making an elongated product such as tubing;

FIG. 29e shows part of the purging cycle of the prior art tip and die process for making an elongated product such as tubing;

FIG. 29f shows part of the production cycle of the prior art tip and die process for making an elongated product such as tubing;

FIG. 31a illustrates by way of example part of the production cycle of the present invention process for making an elongated product such as tubing;

FIG. 31b illustrates by way of example part of the production cycle of the present invention process for making an elongated product such as tubing;

FIG. 31c illustrates by way of example part of the production cycle of the present invention process for making an elongated product such as tubing;

FIG. 31d illustrates by way of example part of the purging cycle of the present invention process for making an elongated product such as tubing;

FIG. 31e illustrates by way of example part of the purging cycle of the present invention process for making an elongated product such as tubing;

FIG. 31f illustrates by way of example part of the production cycle of the present invention process for making an elongated product such as tubing.

DETAILED DESCRIPTION OF THE PREFERRED EMBODIMENTS

In the following description of the preferred embodiments reference is made to the accompanying drawings which form the part thereof, and in which are shown by way of illustration of specific embodiments in which the invention may be practiced. It is to be understood that other embodiments may be utilized and structural and functional changes may be made without departing from the scope of the present invention.

Figure 1:
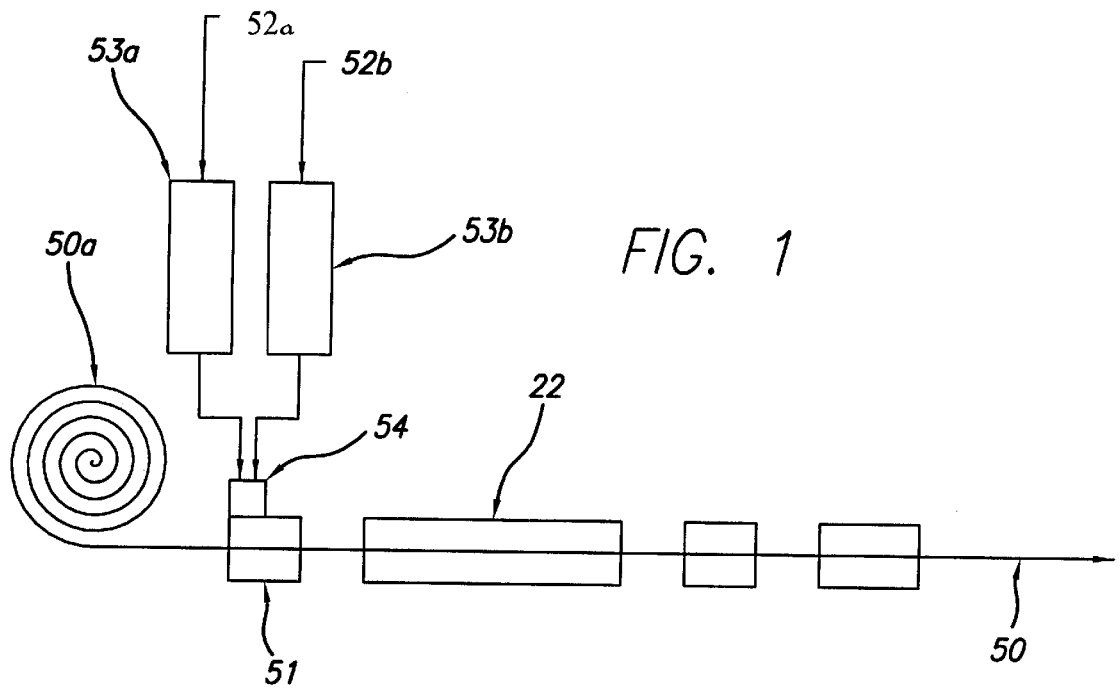
FIG. 1 illustrates a broad structural diagram for the present invention.

An exemplary system of the present invention for making elongated products such as tubing in a tip-and-die assembly with injectors is illustrated in the drawings at FIG. 1. A core 50, such as a continuous wire, is fed from a reel 50a of a wire through a head 51 at a predetermined speed. At the same time, two different polymers, in pellet forms 52a and 52b, are converted into molten polymer streams in two different polymer injectors 53a and 53b respectively. These molten polymers are pushed by the injectors 53a and 53b, one shot at a time, through a flow controller 54 and through the head 51, to form a continuous, multi-polymer jacket around the core, to effectively coat the core. These polymer shots are made in a cyclic, sequential fashion. It is this synchronized, repeating cycles of the polymer shots that keep the polymer jacket continuous on the core 50. The polymer-jacketed core is then cooled down to solidify the polymers, and then measured and collected.

Figure 2:
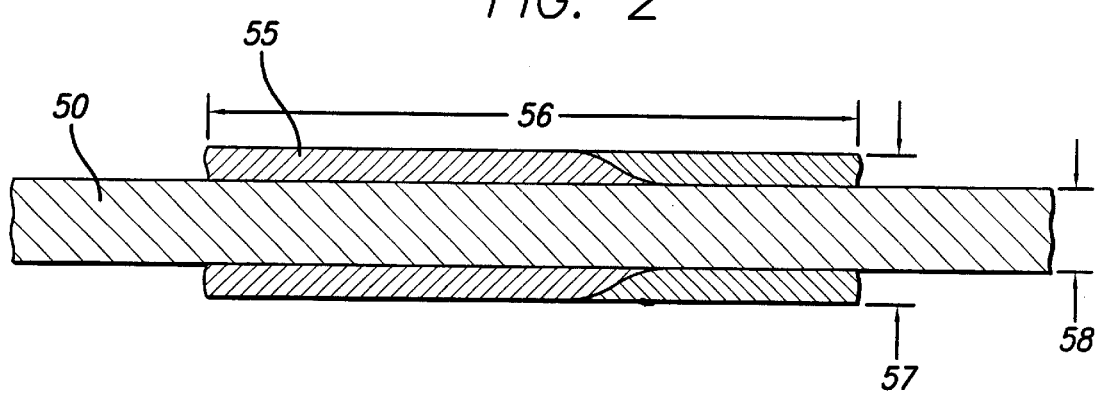
FIG. 2 shows a variable stiffness tubing.

An example is shown in FIG. 2, where the length 56 is sixty inches, the diameter 57 of the product with the polymer jacket 55 is 0.05 inch and the diameter 58 of the core 50 is 0.03 inch.

Figure 3:
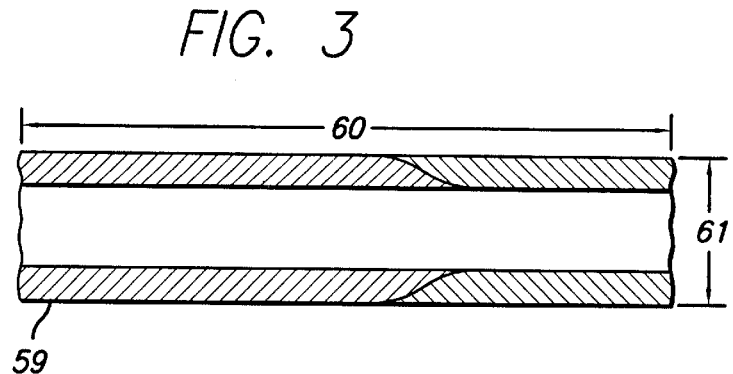
FIG. 3 shows a multi-polymer jacketed core.

In some cases, the cores 50 are subsequently removed to make tubing 59 shown in FIG. 3. For exemplary purposes, the length 60 is seventy inches, and the diameter 61 of the product with the polymer jacket 59 is 0.05 inch.

When the different polymers have different stiffness properties, the article formed would exhibit varied stiffness properties at different sections of the article. The transitions between the stiff and flexible sections are purposely made to be gradual, smooth and non-abrupt, because many applications would require that.

The system is useful for making long articles such as tubing, long variable property articles such as variable stiffness articles, and for these articles with thin polymer walls.

Figure 4:
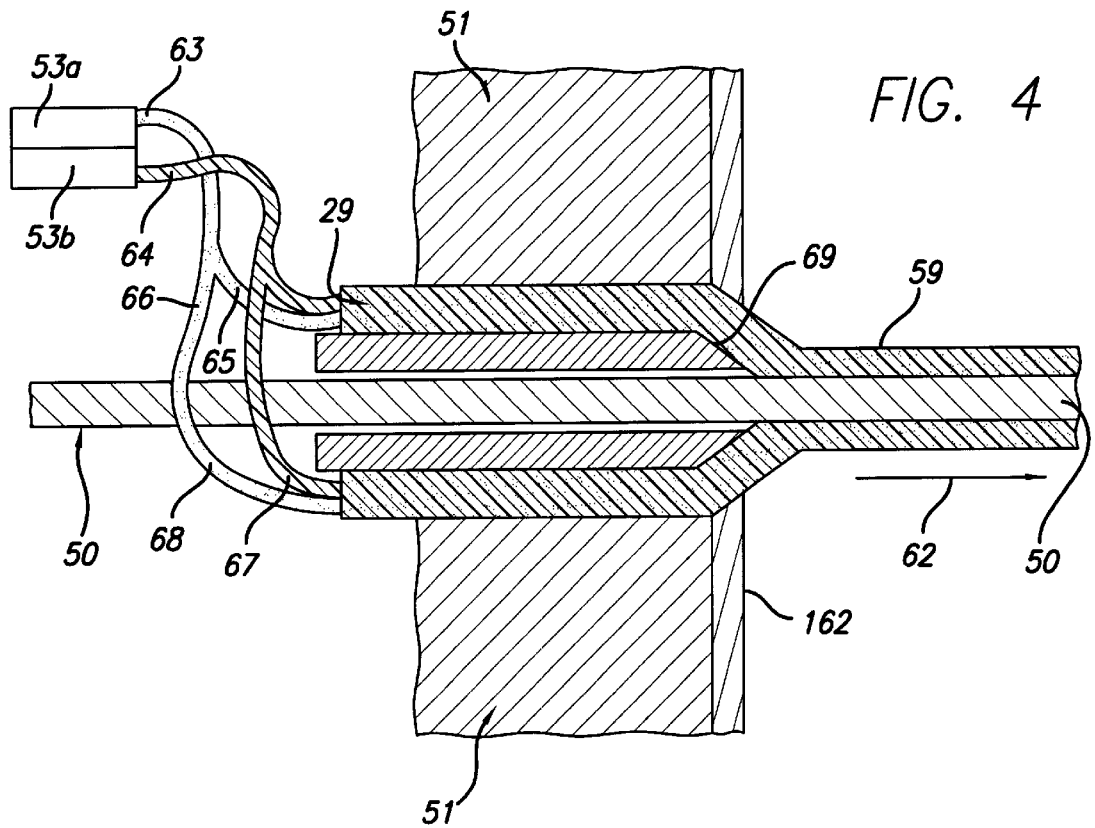
FIG. 4 shows a non-pressure-die tip-and-die head.

In FIG. 4 there is a non-pressure-die-tip-and-die head 62 through which the core 50 and the jacket 59 pass as indicated by arrow 62. The head 51 directs two outlet streams 63 and 64 of the polymer which in turn directed it to branches 65 and 66 and 67 and 68. These streams of polymer are forced to form the jacket 59 around the core 50. As they pass through the die aperture 162 the component 69 is located relative to the die so as to be substantially in line with the face of the outlet.

Figure 5:
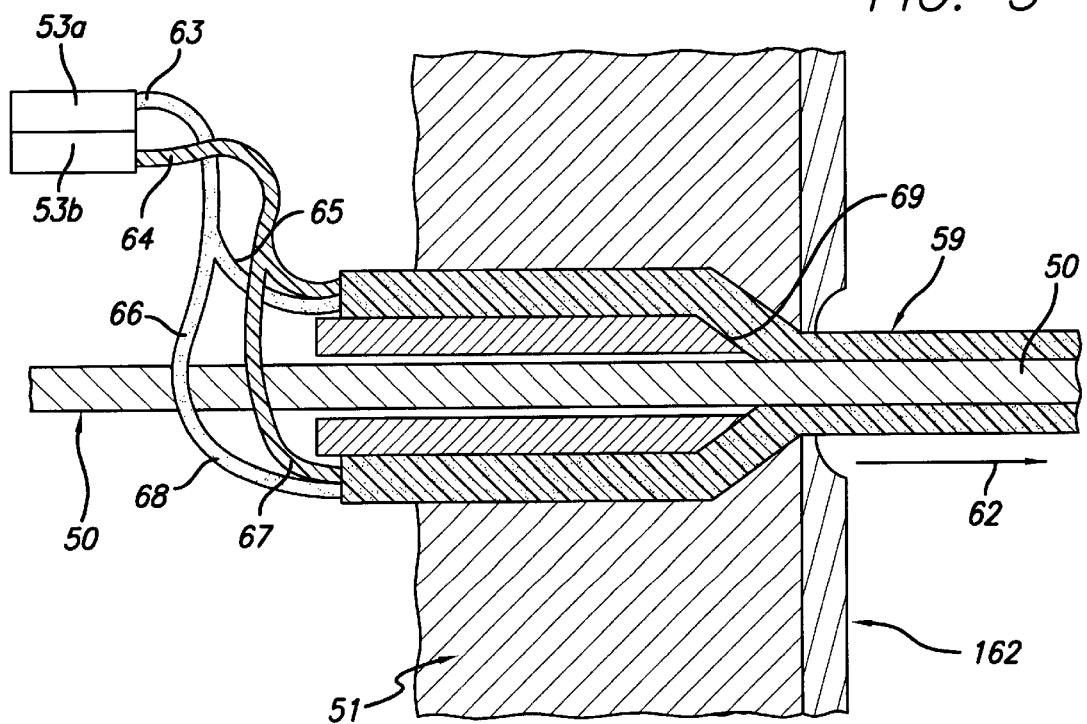
FIG. 5 shows a pressure-die tip-and-die head.

In FIG. 5 as illustrated a pressure-die tip-and-die head similar streams of polymer exit from the die and form the jacket 59 around the core 50. The component 69 which operates in relation to the die aperture are recessed from the aperture such that the jacket-forming operation takes place in a different portion of the die.

The term head 15 in FIGS. 4 and 5 is injected as 53a and 53b polymer into stream 63 and 64. A typical polymer injector 53a or 53b, a reciprocating screw type, is shown in FIG. 6, and its typical operation is shown in FIG. 7. The use of a reciprocating type screw 70 is used for exemplary purposes only. Other types, such as the plunger type, which are well known to those in the art, can also be used.

In step 1 of FIG. 7, the high pressure 72 exerted at the back 71 of the screw 70 forces the screw to move forward to send a shot of molten polymer through the flow controller 54 and to the head 51. In step 2, before the polymer flow is stopped by a flow controller 54, the pressure at the back 71 of the screw 70 is reduced 73, to eliminate the residual flow in the head. After a valve 74 is closed, the screw 70 rotates and slowly moves back to melt additional pellets 52a or 52b to replenish the molten polymer reservoir 75 in front of the screw 70. In a later step the screw 70 stops the rotation and the linear movement, waiting for the next cycle.

In this manner, the polymer either flows through the flow controller 54 and into the head 51 of the tip-and-die assembly, in step 1, or stops flowing completely, as in the other two steps. No material is wasted. There is no bleeding and no messy molten material on the floor.

There are several features in the process that allow the injectors 53a and 53b to be used successfully. The use of two or more injectors allows the injectors to take turns making polymer shots to maintain a continuous polymer jacket on the core.

The injectors are similar to those used in injection molding processes, with some differences. First of all, no mold or platform is used. Next, the injection pressures are much lower in the present invention; namely, 5000 PSI as compared with 20,000 PSI in molding.

In one exemplary embodiment, a singular flow controller 54 is used to handle all material streams 63 and 64 coming from the injectors 53a and 53b.

Figure 8:
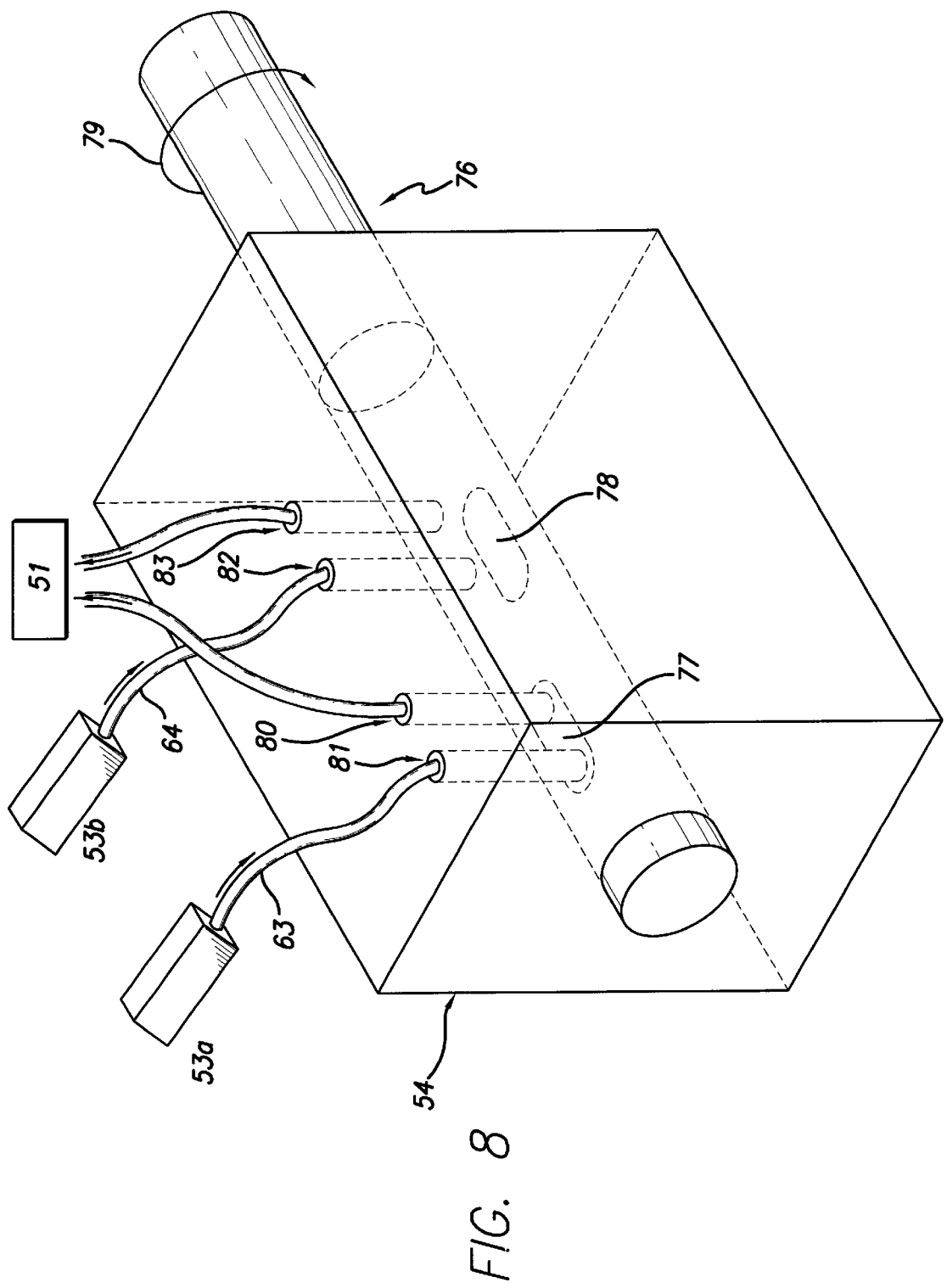
FIG. 8 shows a perspective view of a singular flow controller.

In prior art ILC process, half of the modulators are used for reducing residual flows. In the present invention, those half of the modulators are eliminated by the pressure reduction step 73 of the injectors. This makes it possible to replace the other half of the modulators by a singular flow controller 54, shown in FIGS. 8 through 10.

Figure 9:
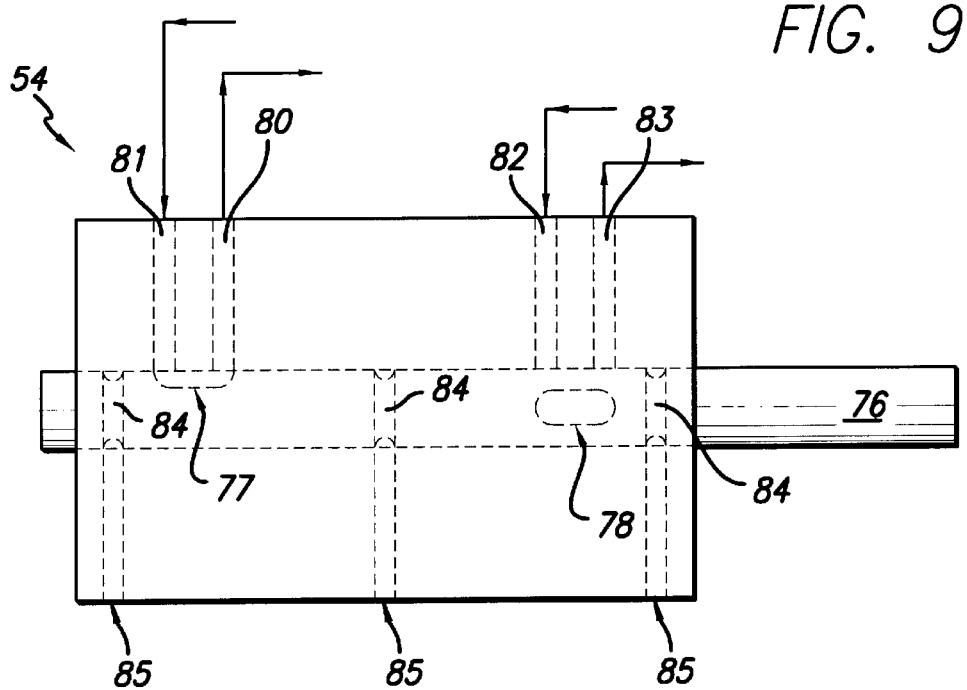
FIG. 9 shows a side view of the singular flow controller in FIG. 8.

The singular flow controller 54 is preferably made of precision-machined metal parts. The shaft 76, with two spaced connecting grooves 77 and 78 respectively that are parallel to the shaft axis, is rotated 79 by a stepping motor or a servo motor, to rotate and stop in a predetermined fashion. The use of a stepping motor or a servo motor is exemplary, as any type of motor to drive the shaft 76 may be used as would be apparent to those skilled in the art. Two sets of holes 80, 81, 82 and 83 are formed in the block of the controller 54 and are connected to the various polymer channels 63 and 64, as shown in FIG. 9.

As the shaft 76 rotates to a position that a connecting groove 77 or 78 matches a set of holes at the upper part of the block, a polymer stream flows through that set of flow channels to the head 51, from an injector 53a or 53b. Otherwise, the flow is shut off. There are three bleeding grooves 84 around the shaft 76 connected to bleeding holes 85 in the block, to prevent leaks from one polymer stream to the other. In other words, instead of having inter-polymer stream leaks, all leaks come out of the bleed holes 85. The injectors 53a and 53b are synchronized with the flow controller 54.

Figure 10:
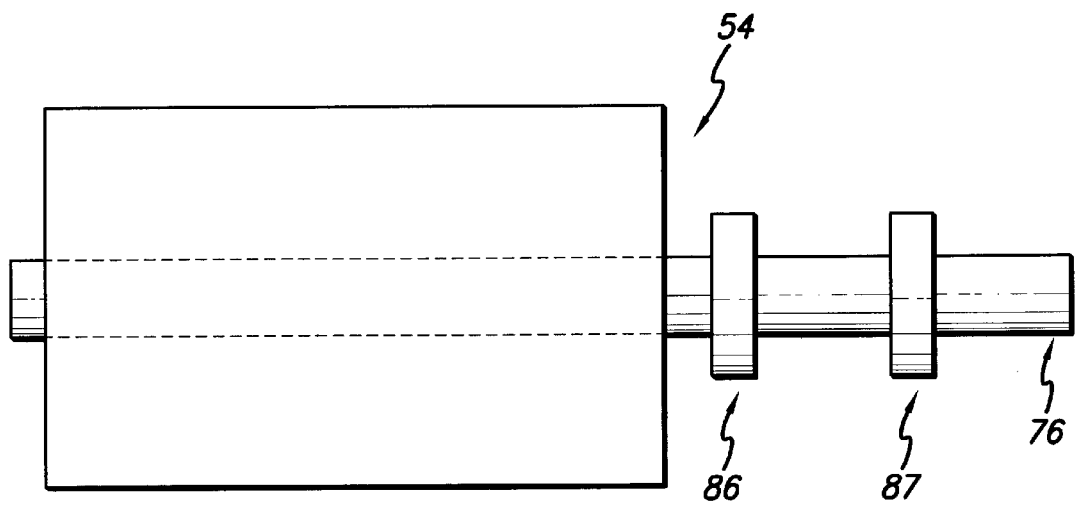
FIG. 10 shows a temperature gradient control for the singular flow controller in FIGS. 8 and 9.

In a further embodiment as shown in FIG. 10, the injector 54 includes a booster heater 86 and a water cooler 87 to create a controlled axial temperature gradient along the shaft 76, to ensure that the block end of the shaft 76 is sufficiently hot for the polymer flow and the motor end of the shaft is cool enough as not to damage the motor.

A variable stiffness tubing with three or more polymers would have a super-pliable transition section. With the use of the singular and reliable flow controller in the present invention, this type of product can be made without the problem of frequent breakdown of modulators in prior art ILC process.

The applications for the super pliable tubing include, but are not limited to, catheters, micro catheters, etc.

Many demanding variable stiffness products, such as medical catheters, have thin polymer walls, ranging from 0.002 inch to 0.02 inch for the single wall thickness. In these applications, the I.D. and O.D. controls are crucial, any excessive fluctuations in polymer output rate is unsatisfactory.

As shown in FIG. 5, when the core 50 moves through the head 51, it drags the polymer with it. The die, with the narrow gap between it and the core, acts like a scraping gate, to limit the amount of polymer carried out by the core. Although the high pressure inside of the die still tends to push out the polymer, the gap is so small that only a limited effect on output is influenced by the pressure. The net result is that, when a pressure die setup is used, as shown in FIG. 5, the polymer output rates are kept steady by the constant speed of the core movement even if an injector is unsteady.

Rate control for the injectors are improved with devices well known in the art such as, but not limited to, a linear voltage to distance transducer.

Figure 11:
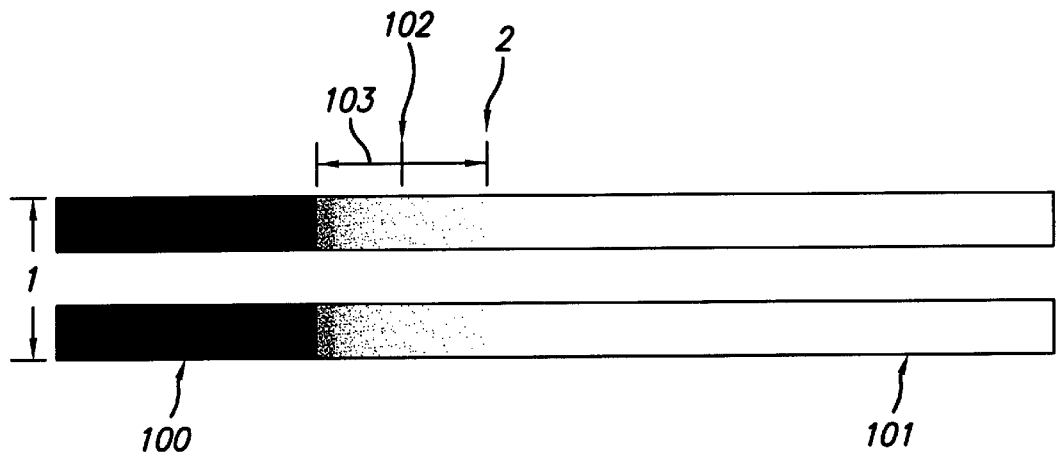
FIG. 11 shows a polymer-blend transitioned variable stiffness tubing utilizing a process of the present invention.
Figure 12:
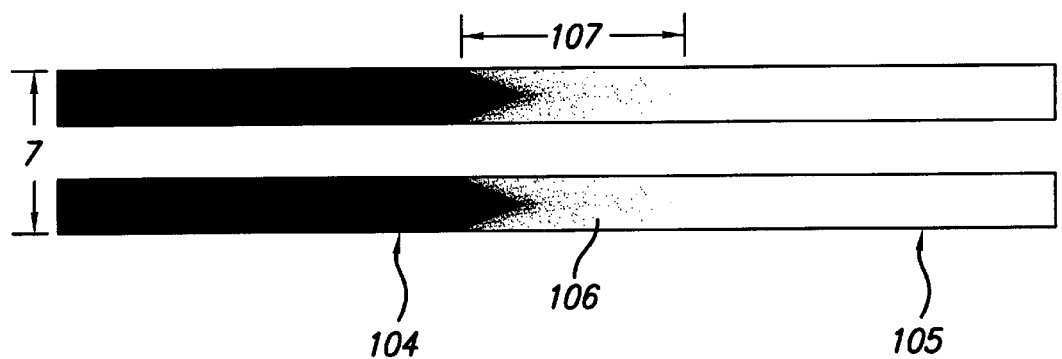
FIG. 12 shows a polymer-blend transitioned variable stiffness tubing, with a wedging effect in the transition section, utilizing a process of the present invention.
Figure 13:
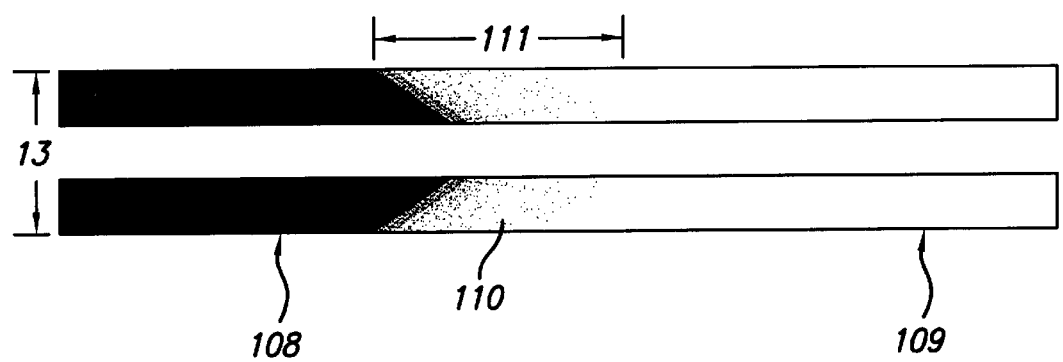
FIG. 13 shows a polymer-blend transitioned variable-stiffness tubing with a tapering effect in the transition section, utilizing a process of the present invention.

FIGS. 11, 12, and 13, show, by way of example, using two materials, where the concentration of the first material gradually changes from nearly 100% at the beginning of the transition to nearly 0% at the end of the transition. In other words, in FIG. 11 the first material 100 is gradually diluted by the second material 101 in a transition area 102. The transition length is defined by the arrow 103. In FIG. 12 the one material 104 makes incisions into a second material 105. The gradual dilution 106 is defined in an area indicated by the arrow 107.

Figure 14:
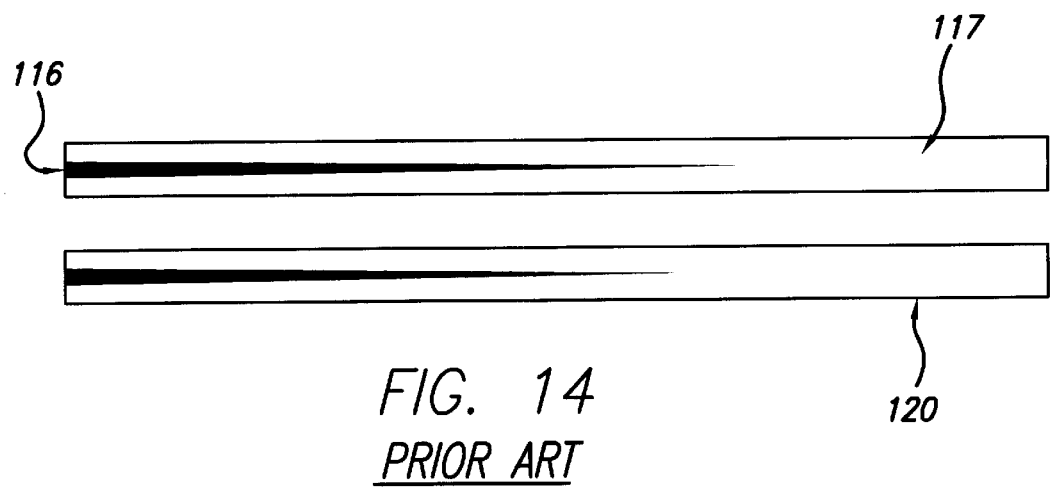
FIG. 14 shows the prior art variable-stiffness tubing with correct proportions.
Figure 15:
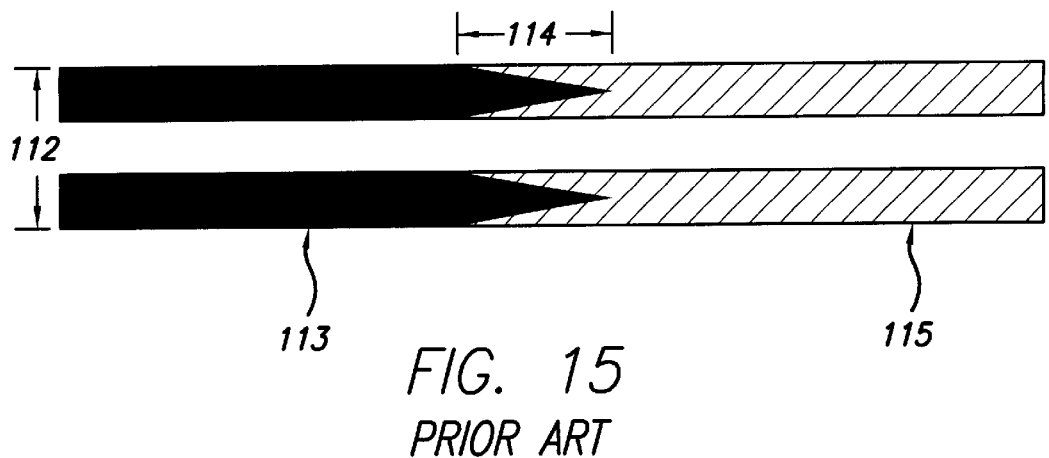
FIG. 15 shows a prior art variable-stiffness tubing where the diameter is enlarged 20 times and the transition section is reduced to ¼ of actual dimensions.
Figure 16:
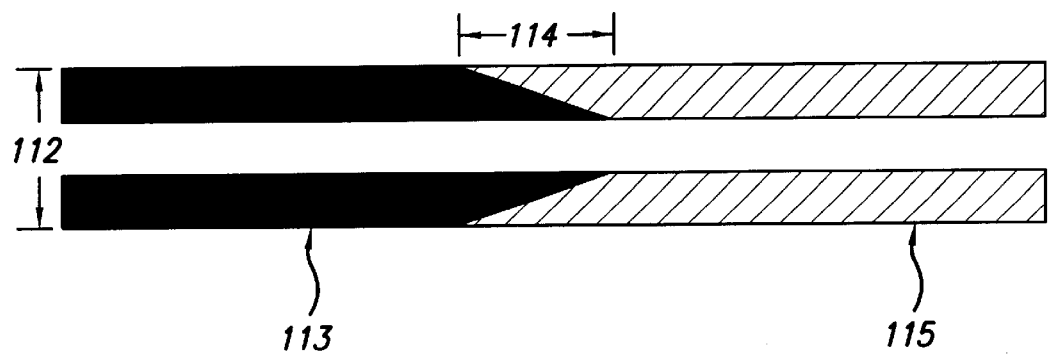
FIG. 16 shows a prior art variable-stiffness tubing where the diameter is enlarged 20 times and the transition section is reduced to ¼ of actual dimensions.
Figure 17:
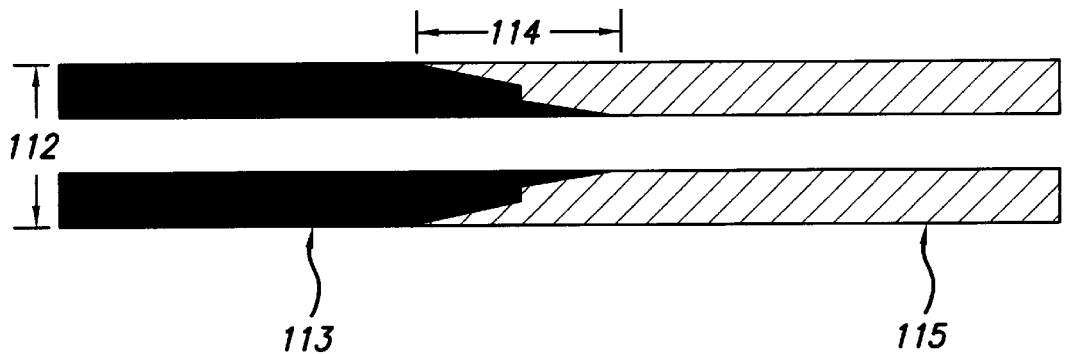
FIG. 17 shows a prior art variable-stiffness tubing where the diameter is enlarged 20 times and the transition section is reduced to ¼ of actual dimensions.

In FIG. 13 the first material 108 is gradually diluted by the second material 109. The dilution area 110 is defined between the arrow 111. In FIGS. 11, 12 and 13, the black dots in the transition sections merely denote the concentration of the stiff polymer, and not the shape of the stiff polymer elements in the blend. Prior art products are shown in FIGS. 15, 16, and 17. In FIGS. 15, 16, and 17, the diameter of the tubing 112 is 0.060 inch. The stiff polymer 113 transitions 114 into the flexible polymer 115. For clarity, the dimensions shown in these figures are not in correct proportions. FIG. 14 shows the thin stiff layer 116 in the correct proportion. The thin stiff layer 116 of the stiff polymer ends at 120. From that point onwards there is only the soft layer of the flexible polymer 117.

Prior art products are shown in FIGS. 14, 15, 16, and 17. In FIGS. 14, 15, 16, and 17, the diameter of the tubing 112 is 0.060 inch. The stiff polymer 113 transitions 114 into the flexible polymer 115. For clarity, the dimensions shown in these figures are not in correct proportions. FIG. 14 shows the thin stiff layer 116 in the correct proportion. The thin stiff layer 116 of the stiff polymer ends at 120. From that point onwards there is only the soft layer of the flexible polymer 117.

Exemplary systems of the present invention for making variable-property products are illustrated in the drawings at FIGS. 18 to 25.

A blending feature involves a relative rotating motion between the tip of the head 121 (FIG. 18) and 122 (FIG. 21) and the housing 123 (FIG. 18) and 124 (FIG. 21) respectively. Rotations for material blending can be done at constant speeds, variable speeds, or intermittently, depending on needs. By way of example relative rotation is accomplished by a relative rotation motion between the tip 121 of the head and a rotating housing 123. In an alternative embodiment, the tip 122 is rotated and the housing 124 is stationary.

Unlike the prior art transition that is formed by the flow pattern of the polymer stream, the product resulting from the present invention is formed by the disruption of the original polymer flow patterns. The different polymer materials thus form an intensely mixed, or confluent mixture.

Figure 18:
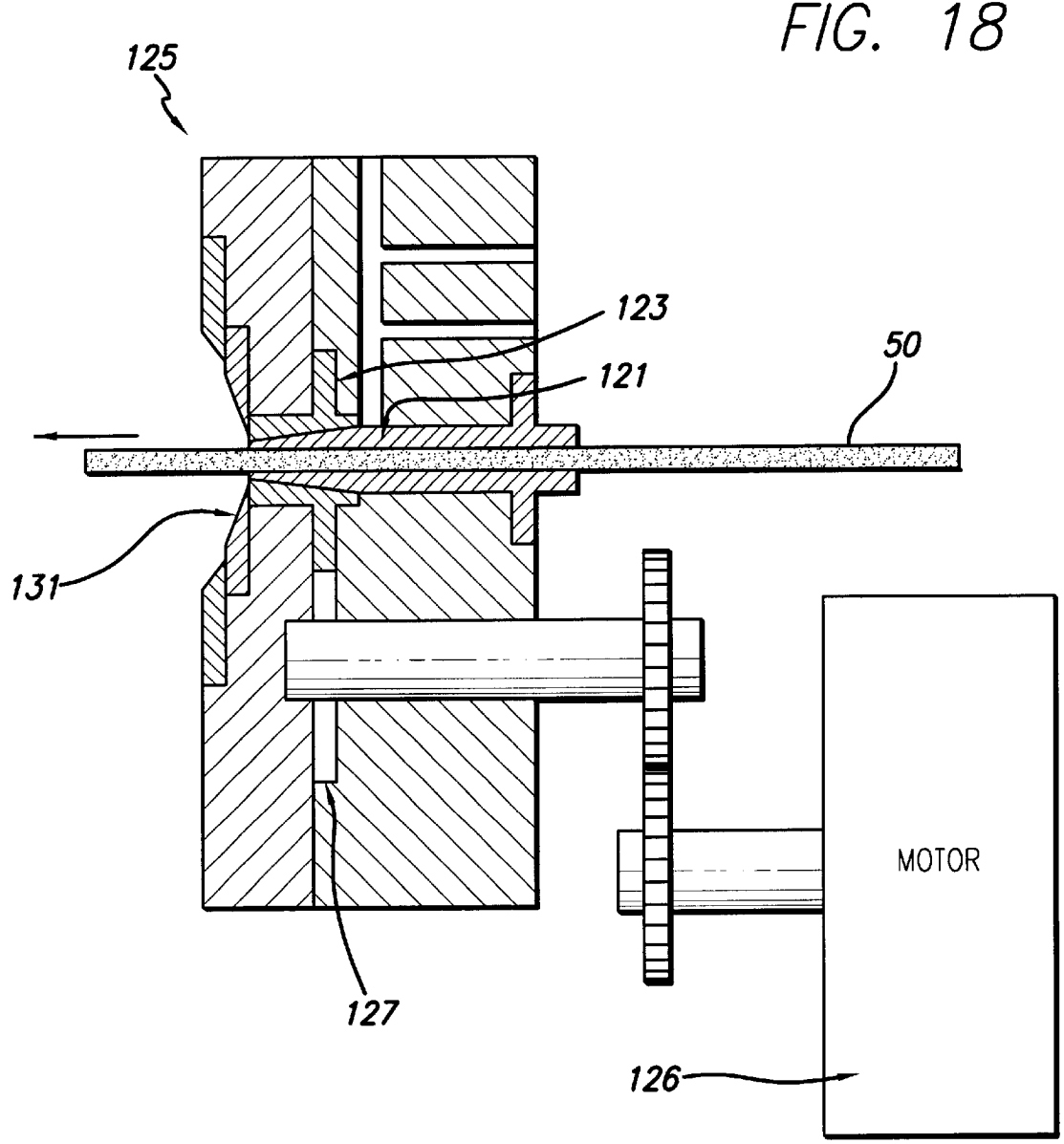
FIG. 18 shows a polymer-blending head with rotating housing.
Figure 19:
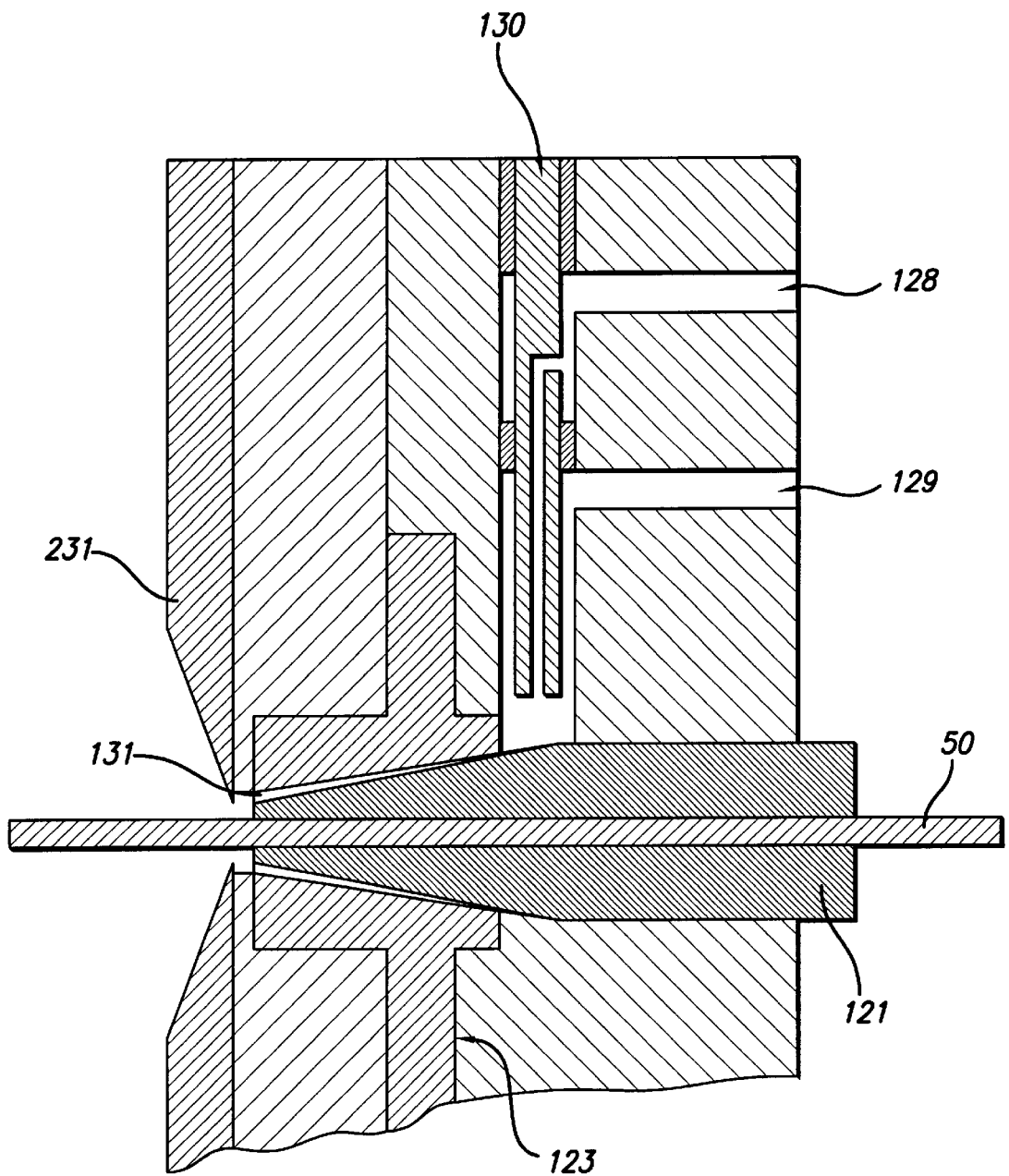
FIG. 19 is an enlarged view of FIG. 8 showing the adjustable tube in the blending head.

FIG. 18 illustrates by way of example, a polymer-blending head 125 with a rotating housing 123. A motor 126 drives a driving gear 127, which rotates the housing 123 around the stationary tip 121. FIG. 19 shows an enlarged view of the adjustable tube in the blending head. Both a flexible polymer and a stiff polymer flow inside 128 and outside 129 of an adjustable tube 130 and into the space 131 in between the stationary tip 121 and the rotating housing 123. The use of two polymers 128 and 129 is for exemplary purposes only. There can be any predetermined number of polymer streams. The polymers are intensely mixed by the relative rotating motion between the stationary tip 121 and the rotating housing 123 before flowing through the die 231 and forming a product such as a medical catheter or electrical wiring with or without a core.

FIG. 20a shows the tip surface 132 of the polymer-blending head. For clarity, the tip is shown opened up and laying flat on its surface. Raised areas, or Bar-like "Bosses" 133 and recessed areas 134 enable the polymer streams to be mixed more intensely. The use of protruding Bar-like "Bosses" 133 and recessed areas 134 are for exemplary purposes only. Many types of well-known methods in the art, such as studs, may be used to mix the materials. FIG. 20b shows the tip surface 135 of the polymer-blending head from a cross-sectional side view, with the raised "bosses" and recessed areas.

A further advantage of the present invention is that in addition to creating a superior transition section for the variable stiffness products, the present invention also allows the transition length to be adjusted during the production, without shutting down the machine and stopping the entire line. This allows the product development efforts to be done in less time than in the prior art. FIG. 19 shows an exemplary adjustable tube 130 which has materials of different properties 128, 129 flowing inside and outside of it. The transition length of the product can be shortened by simply moving the adjustable tube 130 closer to the tip 121.

Figure 21:
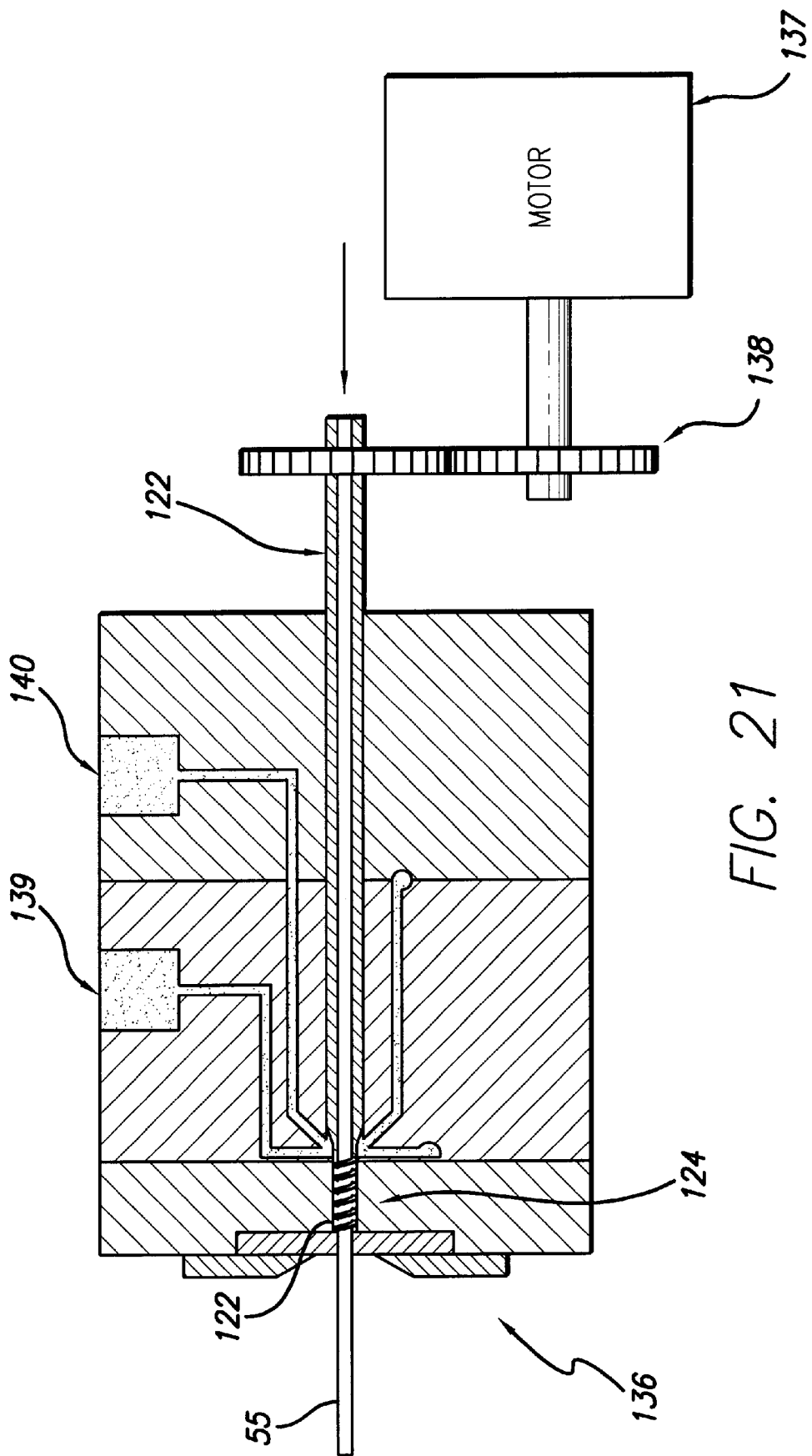
FIG. 21 shows a polymer-blending head with a rotating tip.

FIG. 21 illustrates by way of example, a polymer-blending head 136 with a rotating tip 122. In this exemplary embodiment, a motor 137 and gear 138 directly drives a tip 122 which then rotates relative to the housing. The soft and stiff polymers flow through individual channels 139, 140 and are then mixed by the rotation of the tip.

Figure 22:
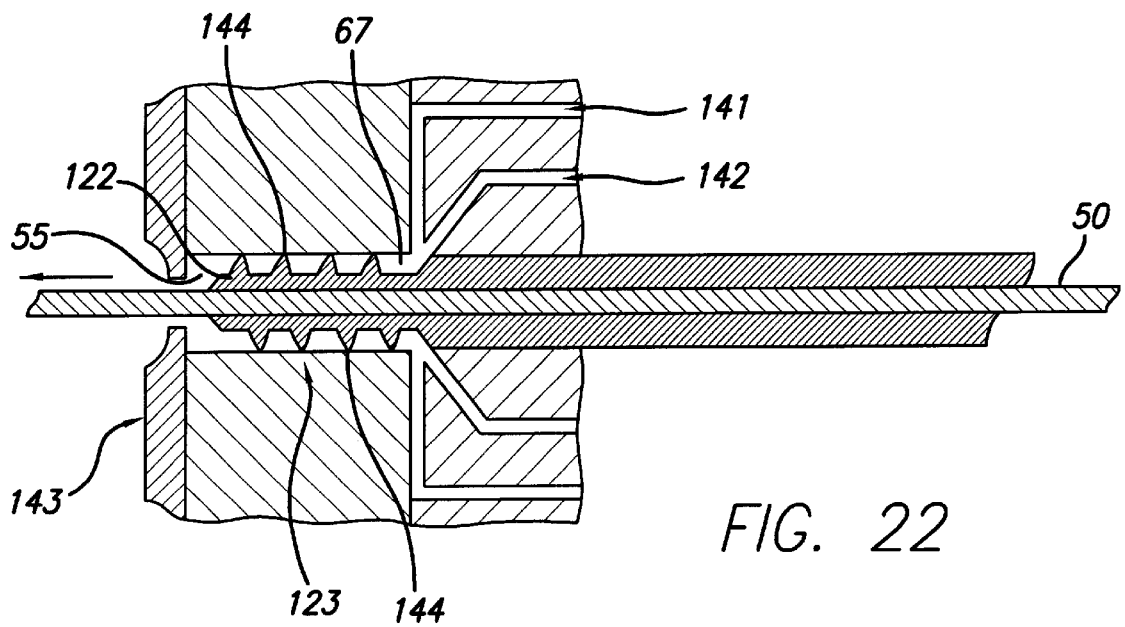
FIG. 22 shows a non-seating version of the head in FIG. 11.

FIG. 22 shows an enlarged view of the tip 122 in the blending head. Both flexible polymer and stiff molten polymer flow through channels 141, 142 and into the space 67 in between the rotating tip 122 and the housing 123. The use of two streams of materials 141 and 142 is for exemplary purposes only. There can be any predetermined number of streams. There is also a core 50 passing through the tip 122.

The polymers are intensely mixed by the relative rotating motion between the rotating tip 122 and the stationary housing 123 before flowing past the die 143 and forming a product such as a medical catheter or electrical wiring.

Pursuant to a preferred embodiment, in FIG. 22 at the portion of the tip where the molten polymer is mixed, there are spiraled grooves 144 which enable the polymer streams to be mixed more intensely.

Figure 24:
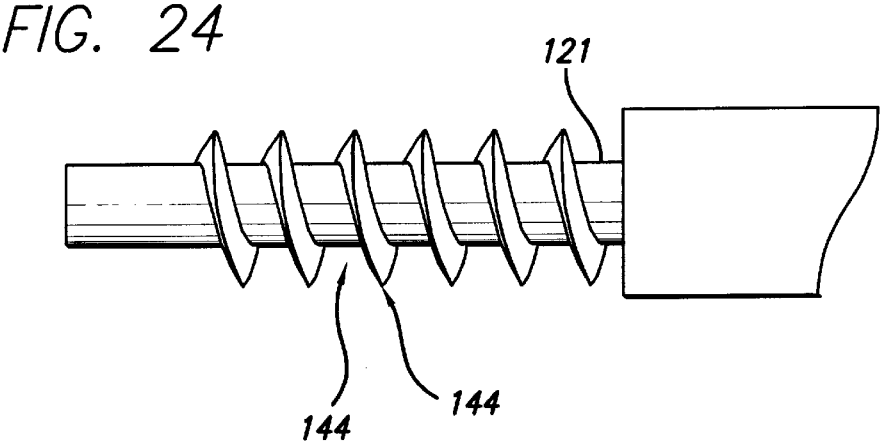
FIG. 24 shows the front end of a rotating tip with a square end for free tubing.
Figure 25:
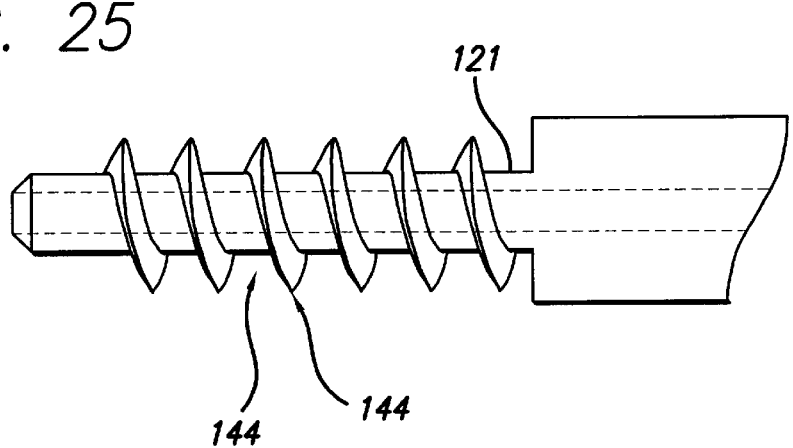
FIG. 25 shows the front end of a rotating tip with a tapered end for over the core operations.
Figure 23:
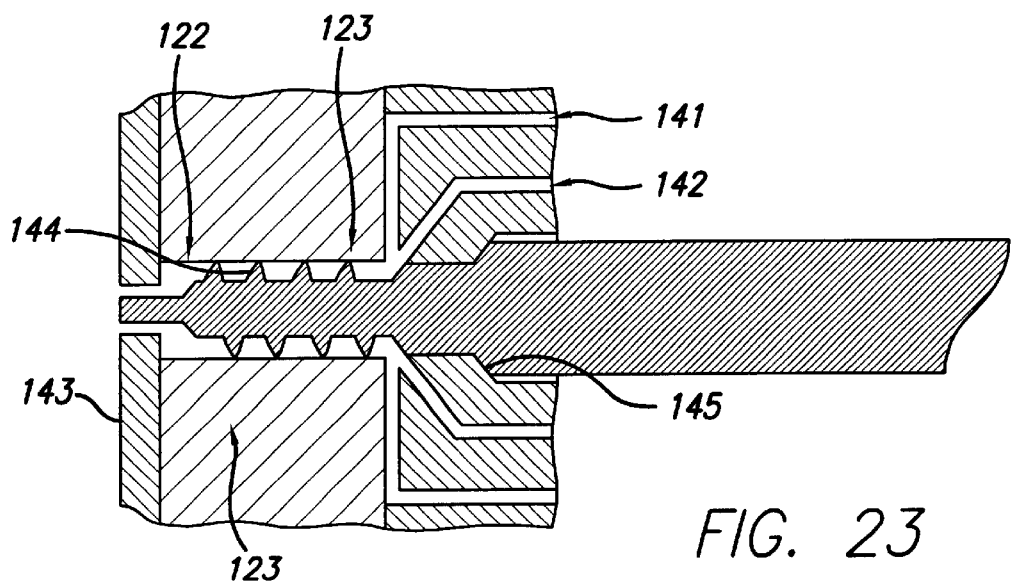
FIG. 23 shows a seating version of the head in FIG. 11.

FIG. 23 shows a seating version of the head in FIG. 22 where the seating area is at 145. FIG. 24 shows the front of a rotating tip 121 with a grooved section where the tip has a square end for making free tubing without a core. FIG. 25 shows the front of a rotating tip with the grooved section 144 where the tip is tapered for over-the-core operations.

When using spiral grooves for polymer blending, as shown in FIGS. 21, 22, and 23, synchronization of rotating speed with that of the extruders is necessary, when the prior art ILC process is used. This may be unnecessary for other processes for making variable stiffness products.

The material mixing refers to the physical mixing of different property materials together, as commonly practiced in the plastics industry for years. Polymer blends are different from solutions such as water and alcohol, where individual molecules of two different compounds can move among each other. In polymer blends, much larger lumps or strands or "rags" of different polymers intermingle with each other. In certain polymer blends, both polymers exist as rags, fiber-like but connected masses. The elements in these masses are so small that they cannot be clearly seen in well-blended polymers through a microscope of low magnification.

However, with a high-powered electron microscope, one should be able to see the elements. For example, in the prior art variable-stiffness tubing, one can clearly see a layer of pure stiff polymer in the transition section of the tubing, as shown in FIG. 14, through a 20× microscope. Through the microscope of the same power, the "stiff layer" in the newly invented product would show a decreasing intensity of the color (for the stiff material) along the axial direction of the tubing, indicating it is gradually diluted with the flexible polymer. This is because the mixture resulting from the present invention is a confluent mixture, or simply, intensely blended together to form a consistent dilution. The prior art product has only regions of pure polymers, but no blends, and no dilution of stiff polymer anywhere.

In further embodiments of the present invention, reinforcements, such as braidings, coils, etc., can be used to enhance the product properties.

A further advantage of the present invention may be the improved torqueability on a tubing resulting from the intensely mixed polymers. The mixing tends to randomize the uneven properties of a tubing, instead of having them along only one side of the tubing to cause a torque transmission barrier, especially when the tubing is bent to a curve.

Although the use of a blending feature which involves a relative rotating motion between the tip of the head and the housing around the tip is discussed throughout this disclosure, other mechanisms to intensely mix the polymers, such as rotating the core, can be used.

Furthermore, although materials with varied stiffness are discussed throughout this disclosure, such as variable-stiffness polymers, products with other varied properties, such as varied surface frictions, can also be made with the present invention.

Figure 26:
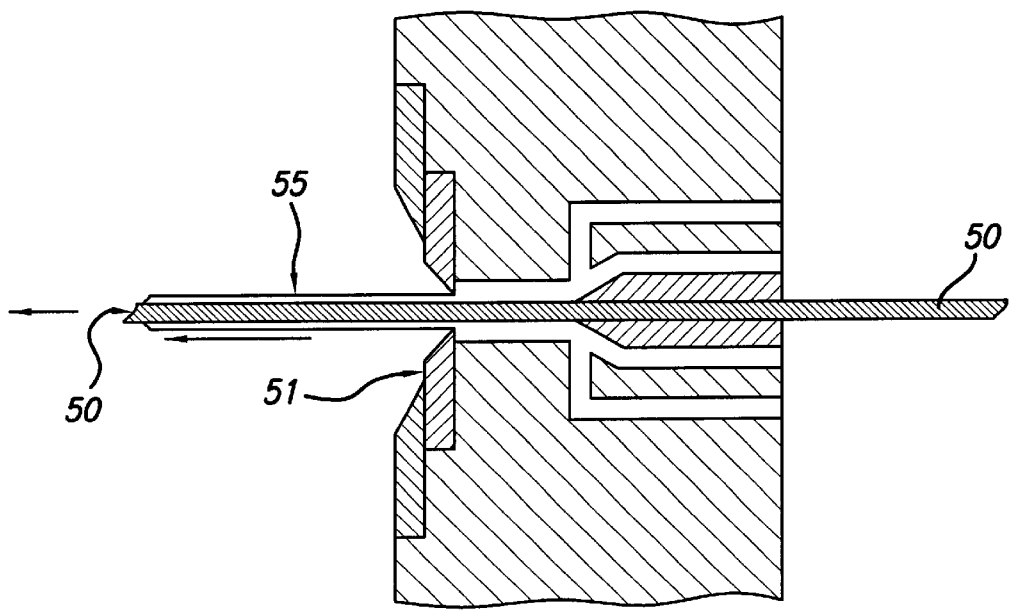
FIG. 26 shows the front end of the head of a prior art tip and die mechanism.
Figure 30:
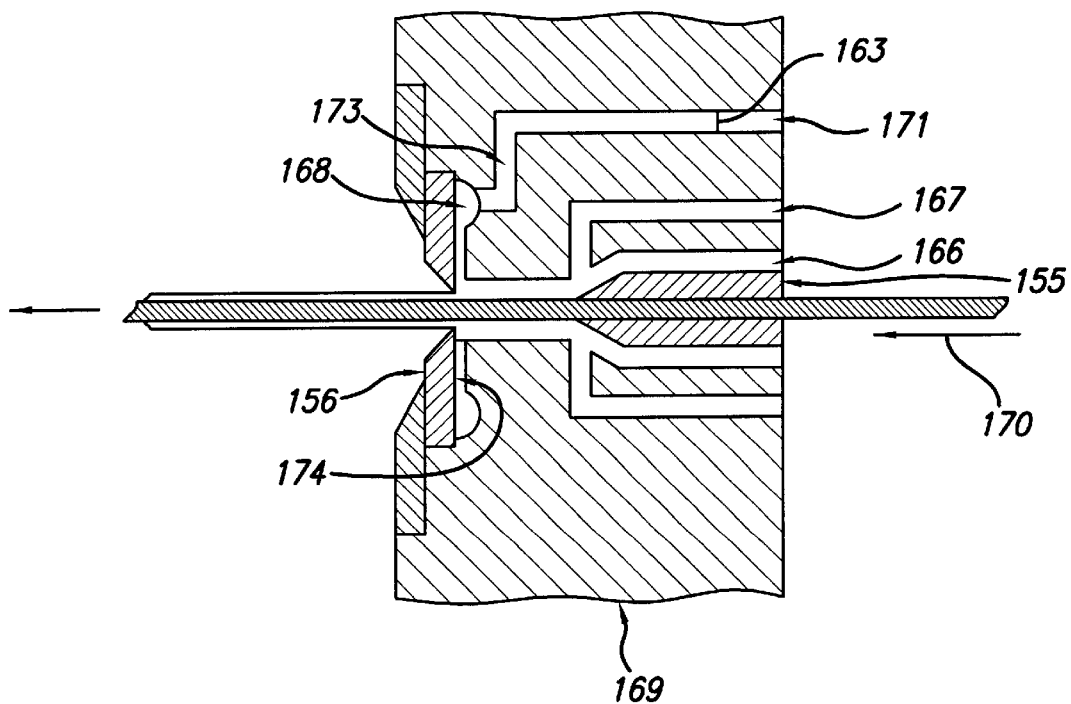
FIG. 30 illustrates by way of example, the front end of the head of a tip and die mechanism in the present invention.

FIGS. 26 and 27 show a prior art tip and die co-extrusion assembly with a pressure die set-up, in operation, with the core 50 moving to the left and the polymers flowing out of the die 51 to form a variable stiffness polymer coating 55 on the core FIG. 27.

Figure 28:
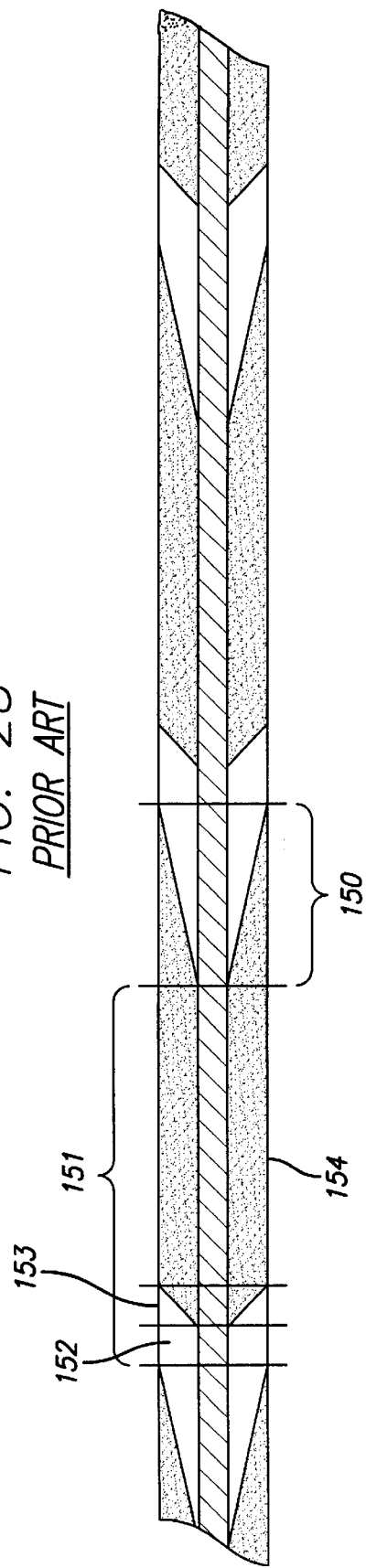
FIG. 28 shows a prior art variable stiffness polymer coated core.
Figure 29A:
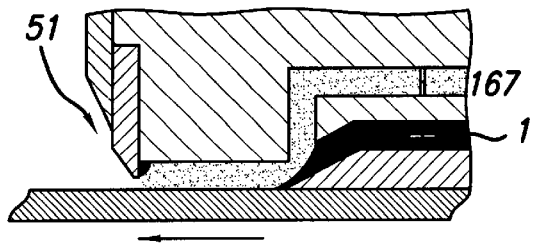
FIGS. 29a–29f shows the complete cycle of the prior art tip and die process for making an elongated product such as tubing.
Figure 29D:
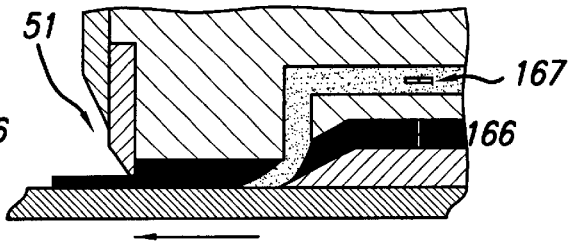
Figure 29B:
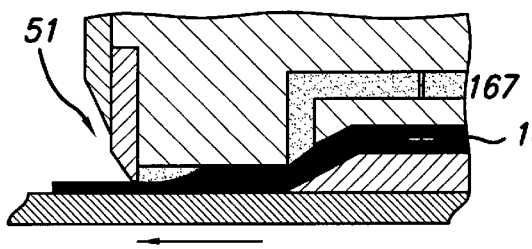
Figure 29E:
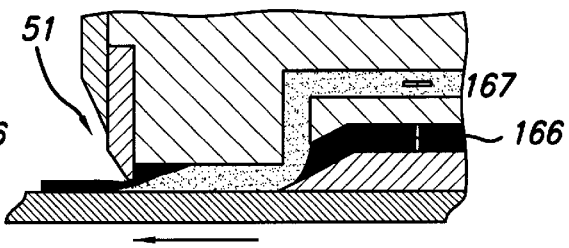

FIGS. 29a–29f shows a complete manufacturing cycle. FIGS. 29a, 29b, 29c and 29e together form the product duration, during which the production portion of the coated core is made. In the case of a catheter production, the product portion of the coated core is then cut out and used as the catheter tubing, after the removal of the core. FIGS. 29d and 29e together form the purging duration, during which the residual stiff polymer is gradually pushed out by the flexible polymer, to get ready for the next cycle. The portion of the coated core generated during the purging duration is the core scrap 150. As shown in FIG. 28, the length 151 includes the portion of the first material 152, transition area 153, and the second material 154.

Figure 31A:
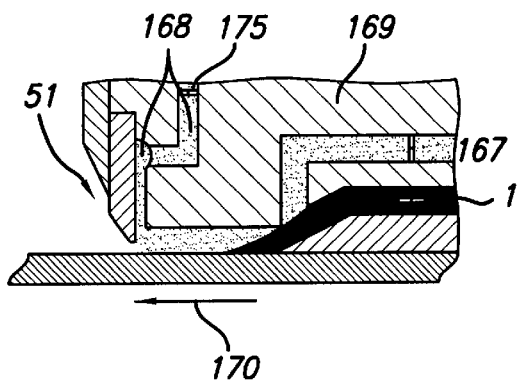
FIGS. 31a–31f illustrates by way of example the complete cycle of the present invention process for making an elongated product such as tubing.

In an exemplary embodiment for reducing core scrap 150, the present invention uses a diverting feature 168 in the head 169 of a tip and die assembly, which diverts a significant amount of material flow through it. FIGS. 31a to 31f show the production process using the present invention. FIGS. 31a, 31b, and 31c are the product duration cycle, that is, when the product is being formed. FIGS. 31a, 31b, and 31c of the process function much like the prior art ILC process shown in FIGS. 29a to 29f. With the present invention there is the purging duration that includes FIGS. 31d and 31e. The diverting feature 168 of the present invention is turned on to divert a significant amount of polymer flow through the diverting feature's channels so that one material flow can run at a high rate to quickly purge out the residual material from. This shortens the purging duration and thus reduces the core scrap. The core speed 170 during the purging may also be decreased, so even less core scrap exists.

Exemplary systems of the present invention for reducing the core scrap 150 in variable-property products are illustrated in the drawings at FIGS. 30 and FIGS. 31a–31f.

A tip 155 and die 156 assembly includes a head 157 with diverting features 168, with channel outlets 171 and also a connecting channel 173. The gap 174 in the head 157 and additional channels 173 are provided in the diverting feature 168 to let part of the polymer flow be diverted through them and discarded and/or re-circulated, during purging of the residual stiff polymer, in the purging process. The use of a polymer flow is for exemplary purposes only. Other materials may be used to form the product in a tip and die assembly. An automatically controlled valve 163 is also provided and synchronized with the functions of the process to open and close the flow channel as desired.

Figure 29C:
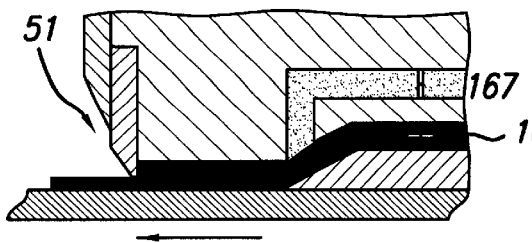
Figure 29F:
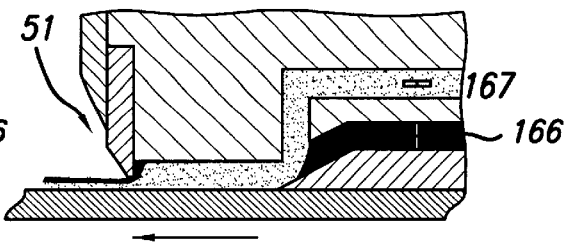

FIGS. 29a to 29f shows the production and purging process in the prior art. In FIG. 29a, the stiff polymer flow starts 166. The flexible polymer is not flowing 167, however, the residual flexible polymer is still completely flowing through the die 51. In FIG. 29b, the stiff polymer flow continues 168, now together with the residual flexible polymer to form the transition section 153. In FIG. 29c, the flexible polymer is not flowing 167, and only the stiff polymer flows through the die 51. The production process for the product is over and then begins the purging process in FIGS. 29d and 29e. In FIG. 29d, the stiff polymer flow stops 166 and the flexible polymer flow starts 167, purging out the stiff polymer through the die 51. As long as the stiff polymer is not fully purged, this portion of the product is waste, or core scrap 150. In the step illustrated in FIG. 29e, the flexible polymer flow continues 167 and the purging continues, until finally purged and only flexible polymer flows through the die. FIG. 29f illustrates the beginning of the new production process.

FIGS. 31a to 31f show a production and purging process of the present invention. FIGS. 31a to 31c are the same as in the prior art except that these are the diverting channels 168. In FIG. 31a stiff polymer flow starts 166. The flexible polymer is not flowing 167, however, the residual flexible polymer is still completely flowing through the die 51. The diverting feature 168 of the present invention is off. Valve 175 is shut. In FIG. 31b, the stiff polymer flow continues 166, now together with the residual flexible polymer to form the transition section 153. The diverting feature 168 of the present invention is still off. Valve 175 is shut. In FIG. 31c, the flexible polymer is not flowing 167, and only the stiff polymer flows through the die 51. The diverting feature is still off.

Figure 31D:
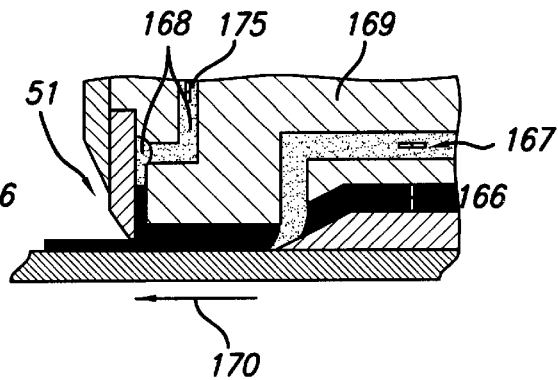
Figure 31B:
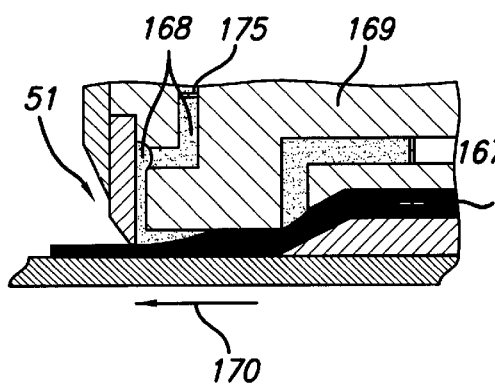

In FIG. 31d, the stiff polymer flow stops 166, and the flexible polymer flow starts 167. The flexible polymer purges out the stiff polymer. As long as the stiff polymer is not fully purged, this portion of the product is waste 150. The diverting feature 168 of the present invention is turned on. Valve 175 is open, allowing a significant amount of polymer flow through the lip purging gap and channels, so that the flexible polymer flow can run at a high rate to quickly purge out the residual stiff polymer, to shorten the purging duration, in order to reduce core scrap.

Figure 31E:
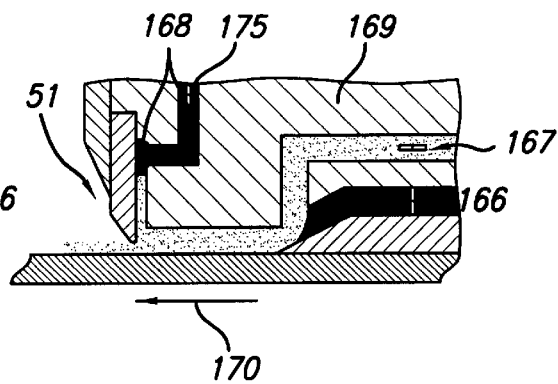
Figure 31C:
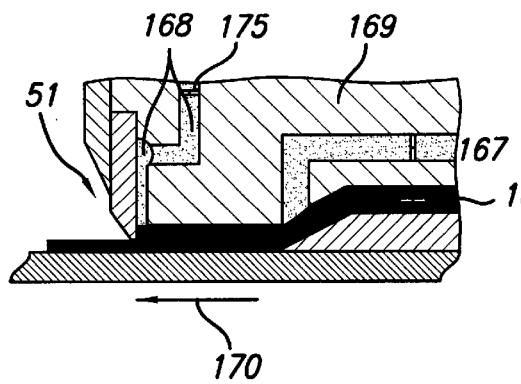
Figure 31F:
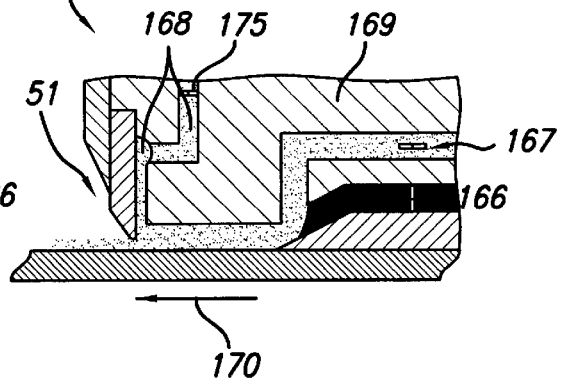

In FIG. 31e, the flexible polymer flow continues at a high rate. Once the stiff polymer is fully purged, the diverting feature 168 of the present invention is turned off, and only flexible polymer flows through the die as shown in FIG. 31f. The core speed 170 during purging FIGS. 31d and 31e, is also decreased, so even less core material is used there.

Figure 32:
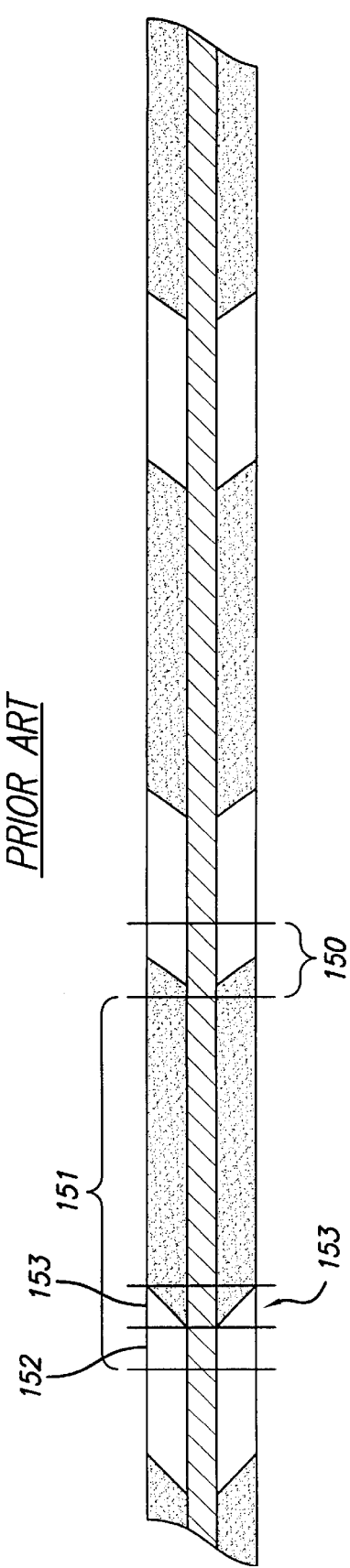
FIG. 32 illustrates by way of example, a variable-stiffness polymer coated core utilizing the present invention.

FIG. 32 shows the much shortened scrap portion 150 for the new coated core 50, made with the present invention. A comparison can be made with the prior art coated core shown in FIG. 28.

During the purging duration, most polymers are allowed to flow through the lip-purging gap, not through the die opening. So, although the polymer flow through the die opening is reduced by slow core speed, the higher polymer flow through the lip purging gap still allows the high polymer flow through the main channel, for the quick purging to take place. This results in a much shorter purging time and a much shorter core scrap section 150 than in the prior art.

The present invention can be carried out at a constant rate of polymer flow, at variable rates, or intermittently, depending on needs. In some cases, at least a part of the diverted flow can be re-circulated. Also the present invention can potentially be applied to the manufacture of free tubing (without a core), for changing the transition on-the-fly and for other purposes.

A further advantage of the present invention is that it enables the adjusting of the transition length of the variable property products on the fly, by having the diverting feature 83 turned on during the product duration of the production process (FIGS. 31a to 31c) and by adjusting the flow rate of the diverted flow.

Yet another advantage of the present invention is to make the flexible section of a variable stiffness product even more flexible, to eliminate a very thin residual stiff layer that usually is left on the surface of the flexible section of a variable stiffness product. This is important for some products such as micro catheters.

The tubes for medical catheter use have for the I.D. a working range of 0.005 to 0.40 inch and a preferred value of 0.008 to 0.20 inch. The O.D. has a working range of 0.01 to 0.50 inch and a preferred value of 0.015 to 0.25 inch. The transition length has a working range of 0.1 to 40 inches and a preferred value of 0.25 to 20 inches. The catheter length has a working range of 4 to 200 inches and a preferred value of 6 to 150 inches.

The tubes in general have for the I.D. a working range of 0.05 to 6 inches and a preferred value of 0.07 to 3 inches. The O.D. has a working range of 0.07 to 7 inches and a preferred value of 0.08 to 3.5 inches. The transition length has a working range of 0.1 to 40 inches and a preferred value of 0.25 to 20 inches.

The electrical cables and wires have for the O.D. a working range of 0.01 to 6 inches and a preferred value of 0.02 to 4 inches. The I.D. (polymer jacket) has a working range of 0.005 to 5.5 inches and a preferred value of 0.008 to 3.75 inches. The transition length has a working range of 0.1 to 40 inches and a preferred value of 0.25 to 20 inches.

Materials that can be used include Nylons (Polyamides), Pebax(s), Polyesters (PET, PBT, etc.) Polyolefins (PE, PP, etc.), Polystyrenes, acrylic polymers, liquid crystal polymers, copolymers and terpolymers of the above, polymer blends of the above, PVCs, and other polymers. Where different materials are to be injected, they can be different materials as listed above or different grades of the same material.

Although materials with varied stiffness are discussed, such as variable-stiffness polymers, products with other varied properties, such as varied surface frictions, can also be made with the present invention.

Medical products of the invention include different fluid supply tubes or catheters. such products comprise a length of a first material having a first stiffness; and a length of a second material having a different stiffness. The two lengths are integrally connected and formed through a process of injection through a die and thereby have a relatively integral elongated combined length defining a portion.

In other forms the product is a consumer product such as an electrical cable, hose pipe, compression fitting, heat shrinkable tube, or shoe lace.

Alternatively the product is artifical turf or fabric. The two lengths are integrally connected and formed through a process of injection through a die and thereby having a relatively integral elongated combined length defining a portion. The combined integral length portions having multiple other portions arranged in side by side relationship thereby to form the artificial turf or fabric.

Applications of the manufacturing processes of the invention and the forming product of the invention using the invented variable stiffness include non-medical products and different medical related products. The medical products are a variety of catheters and other instruments and medical product delivery instruments, pipes and tubes which require the variable properties and characteristics of the product formed by the invention.

Such electric products include strain-relieved electrical cords and cables. Such cords can be foldable, and they include magnetic communication cables, and can be electric cables for printers and computers.

The invented application are for "soft tubing" for "quick-connect" compression fittings. "Quick-connect" compression fittings, such as Swagelock (™) fittings, are widely used in various industries, especially in applications that demand high performances. Prior to the present invention, only rigid tubing can be used with these fittings due to the connecting mechanisms. With the present invention "soft tubing" with rigid ends, made with invented technology is used with these compression fittings. The "soft tubing" can resist kinking and deformation, making them more user-friendly. The use of the invented tubings can vastly expand the application fields of compression fittings.

Another use of the invented technology is in user-friendly "heat-shrinks". "Heat-shrinks" or short heat-shrinkable tubing sections, are widely used in computer hardware, networking, and other areas to connect electrical wires. Heat shrinks can reduce kinking, improve sealing, thus reducing corrosion, and are generally more user-friendly. Such applications can be for connecting electric components and for cable assemblies for instance, in hairdryers.

Yet another application relates to "soft-tipped" artificial turfs. By using "soft-tipped" artificial grass, based on the invented methodology, the artificial turf is more athlete-friendly, less injury-prone, etc.

Still another form of us of the invention is in "velvet-like" fabrics. Textile fibers (the "chopped fibers" type), with soft tips made by the invented technology leads to fabrics that are ultra-soft to the touch, creating a "velvet-like" feel, yet still extremely durable for rough wear-and-tear, etc. "Humane" fur made with invented material is a new class of non-animal fur that is softer than sable, and that can stand −40 degree arctic weather, and can be created with soft-tipped fibers made with invented technology.

The invention also covers "children and senior-friendly" shoelaces. Easy-to-use shoelaces include the advantages that they:

a) can easily be threaded through eyelets;
b) need only light finger-strength to manipulate them;
c) do not come loose by themselves when knotted.

The variable stiffness based shoelaces would have stiff ends for going through eyelets, flexible middle section for making knots, and the carefully controlled surface friction so that they can be easily pulled, loosened by hands but that the knots will stay tightened during use.

Another invented use is non-kinking garden hoses and other tubing products and electrical extension cords. Another characteristic of such invented tubings is that they can easily be bundled up for storage, and as such are useful garden hose and electrical extension cords.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

While the specification describes particular embodiments of the present invention, those of ordinary skill can devise variations of the present invention without departing from the inventive concept.

I claim:

1. A tubular product, comprising:
   a first tubular section of a first material having a first stiffness;
   a second tubular section of a second material have a second stiffness;
   a material blend transition tubular section connecting the first tubular section to the second tubular section
   the transition tubular section being comprised of a mix of the first and second materials; and
   wherein the concentration of the first material gradually changes from nearly 100% at a first end of the transition tubular section to nearly 0% at an opposite second end of the transition tubular section.

2. The product of claim 1 wherein the mix is a confluent mix.

3. The product of claim 1 wherein the first, second and transition tubular sections have a relatively integral elongated combined length.

4. The product of claim 1 wherein the first and transition tubular sections are integrally connected together and the second and transition tubular sections are integrally connected together.

5. The product of claim 1 wherein the first and second materials are different materials.

6. The product of claim 1 wherein the first and second materials are different grades of the same material.

7. The product of claim 1 wherein the first and second materials are different polymers.

8. The product of claim 1 wherein the first material is gradually diluted by the second material in the transition tubular section.

9. The product of claim 1 wherein the first, transition and second tubular sections are formed through a process of injection through a die.

10. The product of claim 1 wherein the first stiffness is stiffer than the second stiffness, and wherein in the transition tubular section and in the direction of the product, the concentration of the first material changes gradually from nearly 100% to nearly 0% and the concentration of the second material changes from nearly 0% to nearly 100%.

11. The product of claim 10 wherein the first and second materials are different materials.

12. The product of claim 10 wherein the first and second materials are different grades of the same material.

13. The product of claim 12 wherein the tubular sections have walls whose thicknesses are between 0.002 to 0.2 inch.

14. The product of claim 1 wherein the tubular sections define a fluid supply tube or a catheter.

15. The product of claim 1 wherein the first, transition and second tubular sections form at least a portion of a medical product.

16. The product of claim 15 wherein the medical product is a fluid supply tube.

17. The product of claim 15 wherein the medical product is a catheter.

18. The product of claim 1 wherein the tubular sections form at least a portion of a consumer product, which is selected from the group of electrical cable, hose pipe, compression fitting, heat shrinkable tube and shoe lace.

19. A tubular product, comprising:
a first tubular section of a first material having a first stiffness;
a second tubular section of a second material having a second stiffness;
a material blend transition tubular section connecting the first tubular section to the second tubular section;
the transition tubular section being comprised of a mix of the first and second materials; and
wherein the first material is gradually diluted by the second material in the transition tubular section.

20. The product of claim 19 wherein the mix is a confluent mix.

21. The product of claim 19 wherein the first, second and transition tubular sections have a relatively integral elongated combined length.

22. The product of claim 19 wherein the first and transition tubular sections are integrally connected together and the second and transition tubular sections are integrally connected together.

23. The product of claim 19 wherein the first and second materials are different materials.

24. The product of claim 19 wherein the first and second materials are different grades of the same material.

25. The product of claim 19 wherein the first and second materials are different polymers.

26. The product of claim 19 wherein the first, transition and second tubular sections are formed through a process of injection through a die.

27. The product of claim 19 wherein the first stiffness is stiffer than the second stiffness, and wherein in the transition tubular section and in the direction of the product, the concentration of the first material changes gradually from nearly 100% to nearly 0% and the concentration of the second material changes from nearly 0% to nearly 100%.

28. The product of claim 27 wherein the first and second materials are different materials.

29. The product of claim 27 wherein the first and second materials are different grades of the same material.

30. The product of claim 29 wherein the tubular sections define a fluid supply tube or a catheter.

31. The product of claim 29 wherein the tubular sections have walls whose thicknesses are between 0.002 to 0.2 inch.

32. The product of claim 19 wherein the first, transition and second tubular sections form at least a portion of a medical product.

33. The product of claim 32 wherein the medical product is a fluid supply tube.

34. The product of claim 32 wherein the medical product is a catheter.

35. The product of claim 19 wherein the tubular sections form at least a portion of a consumer product, which is selected from the group of electrical cable, hose pipe, compression fitting, heat shrinkable tube and shoe lace.

36. A tubular product, comprising:
a first tubular section of a first material having a first stiffness;
a second tubular section of a second material having a second stiffness;
a material blend transition tubular section connecting the first tubular section to the second tubular section;
the transition tubular section being comprised of a mix of the first and second materials; and
wherein the first stiffness is stiffer than the second stiffness, and wherein in the transition tubular section and in the direction of the product, the concentration of the first material changes gradually from nearly 100% to nearly 0% and the concentration of the second material changes from nearly 0% to nearly 100%.

37. The product of claim 36 wherein the first and second materials are different materials.

38. The product of claim 36 wherein the first and second materials are different grades of the same material.

39. The product of claim 38 wherein the tubular sections define a fluid supply tube or a catheter.

40. The product of claim 36 wherein the mix is a confluent mix.

41. The product of claim 36 wherein the first, second and transition tubular sections have a relatively integral elongated combined length.

42. The product of claim 36 wherein the first and transition tubular sections are integrally connected together and the second and transition tubular sections are integrally connected together.

43. The product of claim 36 wherein the first and second materials are different materials.

44. The product of claim 36 wherein the first and second materials are different grades of the same material.

45. The product of claim 36 wherein the first and second materials are different polymers.

46. The product of claim 36 wherein the first, transition and second tubular sections are formed through a process of injection through a die.

47. The product of claim 36 wherein the tubular sections have walls whose thicknesses are between 0.002 to 0.2 inch.

48. The product of claim 36 wherein the first, transition and second tubular sections form at least a portion of a medical product.

49. The product of claim 48 wherein the medical product is a fluid supply tube.

50. The product of claim 48 wherein the medical product is a catheter.

51. The product of claim 36 wherein the tubular sections form at least a portion of a consumer product, which is selected from the group of electrical cable, hose pipe, compression fitting, heat shrinkable tube and shoe lace.

52. The product of claim 36 wherein the concentration of the second material in the transition tubular section changes gradually from nearly 0% to nearly 100%.

* * * * *